(12) United States Patent
Seymour et al.

(10) Patent No.: US 7,279,318 B1
(45) Date of Patent: Oct. 9, 2007

(54) MODIFICATION OF BIOLOGICAL ELEMENTS

(75) Inventors: Leonard C. W. Seymour, Birmingham (GB); Kerry David Fisher, Birmingham (GB)

(73) Assignee: Hybrid Systems Limited, Birmingham (GB)

( * ) Notice: Subject to any disclaimer, the term of this patent is extended or adjusted under 35 U.S.C. 154(b) by 604 days.

(21) Appl. No.: 10/009,347

(22) PCT Filed: Jun. 9, 1999

(86) PCT No.: PCT/GB00/02239

§ 371 (c)(1),
(2), (4) Date: Jun. 26, 2002

(87) PCT Pub. No.: WO00/74722

PCT Pub. Date: Dec. 14, 2000

(30) Foreign Application Priority Data

Jun. 9, 1999 (GB) ................................. 9913359.7

(51) Int. Cl.
*C12N 7/00* (2006.01)
(52) U.S. Cl. ..................................... 435/235.1; 530/350
(58) Field of Classification Search ............. 435/320.1, 435/235.1, 4, 6; 514/44; 536/23.1; 424/93.1
See application file for complete search history.

(56) References Cited

U.S. PATENT DOCUMENTS 5,521,291 A * 5/1996 Curiel et al. .............. 530/391.7
5,656,611 A 8/1997 Kabanov et al.

FOREIGN PATENT DOCUMENTS

WO WO96/21470 6/1996
WO WO98/441143 A1 * 10/1998

OTHER PUBLICATIONS

Verma et al., Nature, vol. 389, 1997, pp. 239-242.*
Anderson, Nature, vol. 392-supplement, 1998, pp. 25-30.*
Juengst, BMJ, vol. 326, 2003, pp. 1410-1411.*
Robinson et al., "Effect of Polyethylene Glycol Conjugated to DNA-Transfecting Complexes Targeted at the Transferrin Receptor of HeLa Cells" *Drug Delivery* 4:115-119 (1997).
Wolfert et al., "Characterization of Vectors for Gene Therapy Formed by Self-Assembly of DNA with Synthetic Block Co-Polymers" *Human Gene Therapy* 7:2123-2133 (Nov. 10, 1996).
Katayose et al., "Water-Soluble Polyion Complex Associates of DNA and Poly(ethyleneglycol)-Poly(L-lysine) Block Copolymer" *Bioconjugate Chem.* 8:702-707 (1997).

* cited by examiner

*Primary Examiner*—James Ketter
(74) *Attorney, Agent, or Firm*—Pillsbury Winthrop Shaw Pittman, LLP

(57) ABSTRACT

A method of modifying the biological and/or physicochemical properties of biological elements such as viruses and other micro-organisms is disclosed in which the biological element is modified by providing it with a coating of a multivalent polymer having multiple reactive groups. This modification can enable some biological elements to be targeted or re-targeted to particular sites in a host biological system and can be useful in connection with viral vectors for gene therapy or antitumor therapy. In other cases the modification can be useful for enhancing or improving the efficiency of viruses or bacterial micro-organisms used for example in pest control, degradation and dispersal of oil deposits and various other industrial, environment or medical applications.

35 Claims, 13 Drawing Sheets

Figure 4:
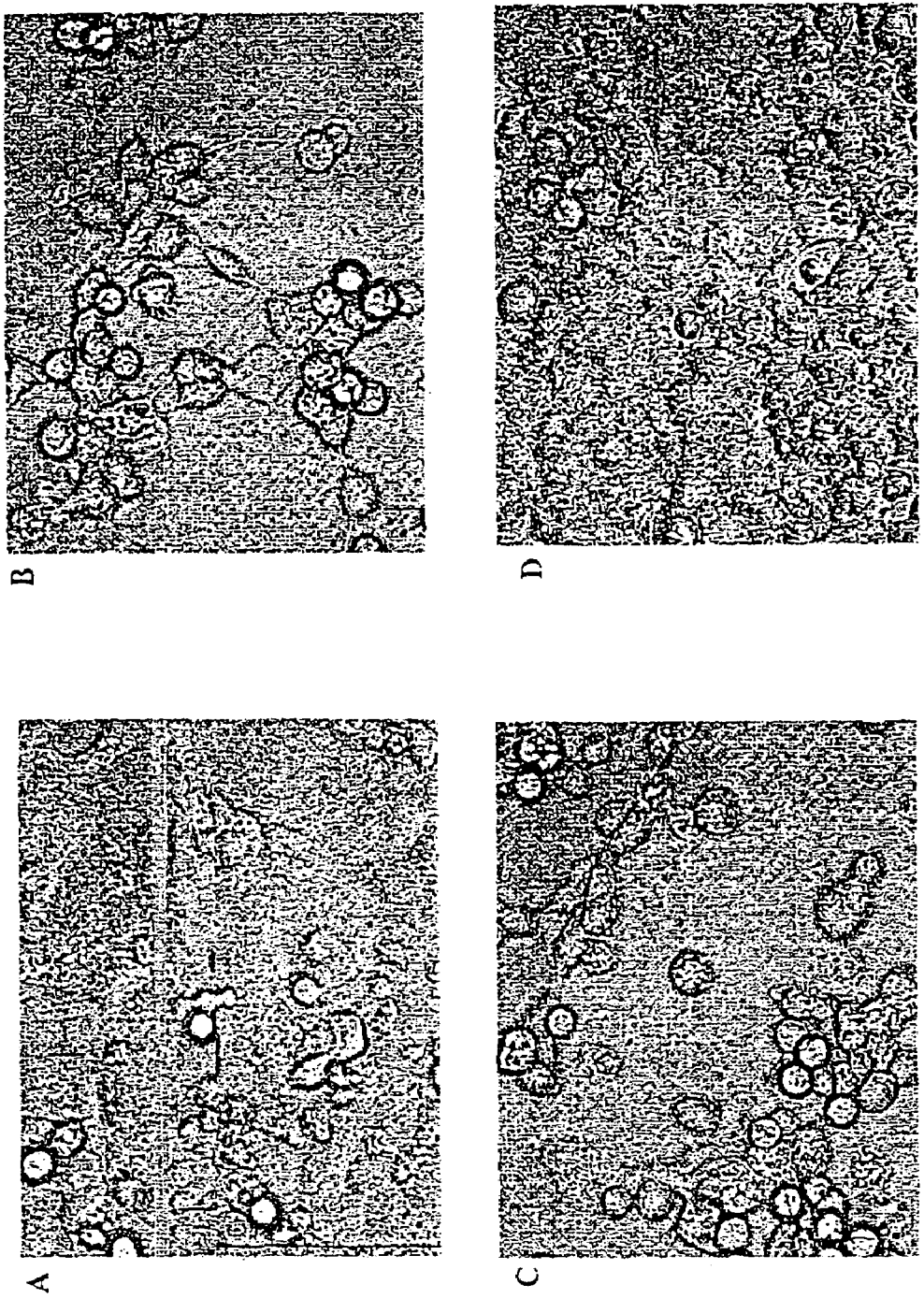

Figure 4. Reduction of cytopathic effect of wt Ad5 by addition of pHPMA-Gly-Gly-ONp Figure 6: Physical Characteristics of pHPMA coated adenovirus

SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: chemically synthesized

<400> SEQUENCE: 1

Gly Phe Leu Gly
1

MODIFICATION OF BIOLOGICAL ELEMENTS

CROSS REFERENCE TO RELATED APPLICATIONS

This application is the National Phase of International Application PCT/GB00/02239, filed Jun. 9, 2000 which designated the U.S., and claims priority from British Patent Application No. 9913359.7, filed Jun. 9, 1999, and which are incorporated herein by reference.

The present invention relates to methods of modifying the biological and/or physico-chemical properties of micro-organisms referred to hereinafter by the collective term "biological elements" of which viruses constitute one important category. The invention also relates to such biological elements which have been modified to bring about a modification or change in their biological and/or physico-chemical properties in accordance with the invention, processes for their preparation and their use in various biotechnology strategies in various fields, including agriculture, the petrochemical industry, environmental science and medicine.

BACKGROUND

Micro-organisms, including viruses, find many applications throughout the broad fields of biotechnology. They are involved in medicine, agriculture, industrial production processes (including notably the oil and brewing industries) and bioremediation. Many useful applications and functions have been identified and developed for such biological agents. However, often the development or enhancement of their activities is limited by their precise properties, restricting their ability to fulfil tasks that are theoretically possible but practically beyond their scope. In this situation, which is quite commonly encountered, it would often be desirable to re-engineer the properties of the virus or micro-organism to endow it with properties more appropriate for its required purpose.

Thus, biological insecticides for example such as baculoviruses may be restricted in their usefulness through inappropriate target specificity and adverse survival characteristics in the environment; sulphur metabolising bacteria may be limited in their useful application in the petrochemical industry through inadequate patterns of dispersion and distribution; and in the context of human or veterinary gene therapy, viruses intended to mediate delivery of therapeutic genes may be limited in their usefulness through inefficiency of transgene expression in target tissues.

The field of somatic cell gene therapy has attracted major interest in recent years because it promises to improve treatment for many different types of disease, including both genetic diseases (e.g. cystic fibrosis, muscular dystrophy, enzyme deficiencies) and diseases resulting from age- or damage-related physiological deterioration (cancer, heart disease, mature onset diabetics). However, although the field has seen rapid and extensive development, including initiation of over 100 clinical trials, instances of clear therapeutic benefit to patients are very few. One antisense technology has recently been licensed for human use, but no gene therapy strategies have as yet fulfilled their original promise and none are likely to be approved for routine clinical application in the foreseeable future.

The reasons for lack of therapeutic efficacy partly reflect the patient population (most patients enrolled for these experimental treatments are already quite sick so that even an effective treatment might show little therapeutic benefit) but primarily reflect the inadequate levels, duration and distribution of expression of therapeutic genes achieved. In short, the successful application of sophisticated treatment strategies is limited by inadequate vectors for gene delivery and expression.

Two main types of vectors for use in gene therapy applications have been explored so far—non-viral (usually based on cationic liposomes) and viral (usually retroviruses, adenoviruses, latterly adeno-associated viruses (aav) and lentiviruses).

Viruses are the obvious choice as vectors for gene delivery since this is essentially their sole function in nature. Consequently viruses have seen considerable use in gene therapy to date, forming the majority of vectors employed in clinical studies. The main feature of adenoviruses which limits their successful application is their immunogenicity. Although they are professional pathogens, evolved over millions of years as highly efficient gene delivery vectors, their hosts have similarly developed very effective protection mechanisms. Serum and ascites fluid from cancer patients contain antibodies that can completely prevent viral infection in vitro even at high dilution. Typical human protocols involving adenovirus lead to significant inflammatory responses, as well as inefficient infection of target cells.

Although the non-viral systems have a much better safety record, and are easier to produce in large quantities, they have low specific transfection activity and efficiency of gene expression in target tissues has been a major problem.

Another major limitation to successful application of presently available vectors for treatment of disease is a requirement for their administration directly to the site of disease, either by direct application or by intra-arterial administration. No vectors are capable of targeting to specific cells following intravenous injection. Cationic lipid systems occlude the first capillary bed they encounter, the pulmonary bed, while adenoviruses/retroviruses are rapidly taken up by the liver and (in animal studies) mediate local toxicities. Although local administration can be feasible for treatment of certain diseases (e.g. bronchial epithelial cystic fibrosis), other diseases have a more widespread distribution (notable clinical cancer and atherosclerosis) and intravenous targeted gene delivery is crucial to embrace the possibility of successful gene therapy.

One approach disclosed in WO 98/44143 for facilitating clinical use of viruses has been to modify the surface of the viruses with a mono-functional polymer such as poly(ethylene-glycol) (PEG). This can lead to significantly decreased neutralisation of infection by serum antibodies. This approach retains normal receptor-binding and infection in respect of target cells (via the CAR receptor for adenovirus), but presents a problem in that it does not facilitate targeting of the virus to selected receptors to gain useful and therapeutically-relevant tropisms.

WO 98/19710 discloses the use of multivalent polymers to coat cationic complexes of nucleic acid material to act as a-carrier vehicle for delivery of the nucleic acid material in biological systems. However, there is no disclosure or suggestion that the polymers would be useful to coat viruses or other micro-organisms.

One object of the present invention is to be able to target the virus or micro-organism to allow completely flexible tropism and modification of biological or physical properties.

Other objects and features of the invention will become apparent from the following more detailed description and Examples.

SUMMARY OF THE INVENTION

From one aspect the invention provides a method of modifying biological and/or physicochemical properties of a biological element, said method comprising reacting said biological element with a multivalent polymer having multiple reactive groups so that the biological element is linked to the polymer, thereby being modified such as to change or modify said biological and/or physicochemical properties.

Where the biological element is an infectious agent such as a virus that normally targets and interacts with particular sites or receptors in a host, the invention can provide a method of modifying the infectivity of such biological element and/or retargeting it to a new or different site or receptor in the host. Such retargeting can provide possibilities for achieving a selectively re-engineered infectivity useful in the case where the biological element is a vector, e.g. a viral vector, containing therapeutic genetic material or an antitumour agent. The re-targeting can be carried out by incorporating a specific targeting group or moiety in the multivalent polymer and by ensuring that after modification the biological element is sufficiently coated with the polymer as to inhibit targeting and interaction with the original target site or receptor of the host.

The invention may also provide a method of modifying the solubility or partition co-efficient characteristics of the biological element in non-aqueous media which can be useful in connection for example with applications of the biological elements in oily media or for improving efficiency of the oil degrading activity of certain oil degrading microorganisms. This can be achieved in some embodiments by incorporating an appropriate hydrophobic group in the polymer and can also be useful for facilitating intra-arterial administration of gene therapy viral vectors in oils.

In some cases where the biological element is a virus having an outer envelope a preliminary step before reacting it with the polymer may comprise stripping off the envelope.

From another aspect the present invention can also be regarded as consisting in a biological element which is modified by being linked to a polymer having multiple reactive groups whereby the biological and/or physicochemical properties of said biological element are modified.

The term "biological element" is used herein to mean bacteria, bacteriophages, fungi, spores (from bacteria or fungi), viruses and viral cores that contain genetic information. For the avoidance of doubt, it will be understood that the term "viral core" refers to a virus that has been treated so as to have an outer surface envelope or capsid of the virus removed.

In many embodiments, the linkage of the polymer to the biological element results in inhibition of the ability of the biological element in a host biological system to interact with other molecules with which it would normally interact, or in inhibition of the ability of the biological element to bind to sites or cell receptors to which it would normally bind in its unmodified state. In the case of biological elements such as viruses which are adapted to target particular sites or receptors when infecting a host, as already indicated it can be possible by means of this invention to retarget such biological elements so as to target different receptors or interact with different targets.

Usually, the polymer will be linked to the biological element by two or more linkages. It has generally been found that at least two linkages are required to obscure a receptor binding site on the biological element.

According to the present invention there is further provided a process for the preparation of a polymer modified biological element in accordance with the present invention which process comprises combining a biological element with a polymer. The invention also provides a polymer modified biological element obtainable by this process.

The invention further provides a polymer modified biological element for in vivo delivery of therapeutic genetic material to a patient, in carrying out gene therapy or DNA vaccination treatment for example, wherein the polymer modified biological element is a polymer modified biological element in accordance with the invention which includes the therapeutic genetic material. It will be understood that the term "therapeutic genetic material" is used therein to denote broadly any genetic material or nucleic acid administered for obtaining a therapeutic effect, e.g. by expression of therapeutically useful proteins or RNA's.

The invention further provides a polymer modified biological element for delivery of biological pesticides such as viral pesticides to pathogens for agricultural use, wherein the polymer modified biological element is a polymer modified biological element in accordance with the invention in which the polymer is selected so as to bring about a modified solubility and improved dispersal and stability of the biological element within the environment and/or so as to achieve greater selectivity of action through targeted interaction with specific hosts.

According to the present invention there is also provided a method of gene therapy which method comprises administering to a patient in need of such therapy a polymer modified biological element in accordance with the present invention which comprises a biological element that includes therapeutic genetic material.

The present invention also provides the use of a polymer modified biological element in accordance with the present invention in the manufacture of a medicament for use in gene therapy wherein the polymer modified biological element comprises a biological element which includes therapeutic genetic material.

The present invention further provides a composition comprising a polymer modified biological element in accordance with the present invention in association with a carrier.

Embodiments of the present invention generally provide a polymer modified biological element wherein the polymer is linked to the biological element by two or more linkages, the polymer used being a multivalent polymer, i.e. it includes multiple reactive groups.

It will be understood that the term "reactive group" is used herein to denote a group that shows significant chemical reactivity, especially in relation to coupling or linking reactions with complementary reactive groups of other molecules.

The polymer used in the present invention is preferably a synthetic hydrophilic multivalent polymer containing a plurality of said reactive groups. In regard, the polymer is a biologically inert polymer. The polymer backbone is generally substituted by said reactive groups. These reactive groups may be connected to the polymer backbone either directly or via a spacer group such as an oligopeptide linkage. Such oligopeptide linkage preferably comprises from 1 to 4 peptide groups, especially 2 or 4. Examples of suitable linkages include -Gly-Gly-, -Glu-Lys-Glu-; and -Gly-Phe-Leu-Gly- (SEQ ID NO:1).

The polymer backbone is preferably based upon monomer units such as N-2-hydroxypropylmethacrylamide (HPMA), N-(2-hydroxyethyl)-1-glutamine (HEG), or ethyleneglycololigopeptide. Where the backbone is based upon ethyleneglycol-oligopeptide, the oligopeptide group preferably comprises from 1 to 4 peptide groups. It is the oligopeptide group which is substituted by the reactive group, optionally via a spacer group as defined above.

A suitable reactive group for the polymer is a group which will react with a group, e.g. an amino group, already present on the surface of the biological element. For example p-nitrophenol (ONp) esters or N-hydroxysuccinimide (NHS) esters could be used.

Examples of suitable polymers for use in the invention are disclosed in WO 98/19710 and include polyHPMA-GlyPheLeuGly-ONp, polyHPMA-GlyPheLeuGly-NHS, polyHPMA-Gly-Gly-ONp, polyHPMA-Gly-Gly-NHS, poly (pEG-oligopeptide(-ONp)), poly(pEG-GluLysGlu(ONp)), pHEG-ONp, pHEG-NHS. The preparation of these compounds is disclosed in WO 98/19710. The contents of WO 98/19710 is included herein by reference.

In some instances the polymer and/or the linkages between it and the biological element are optionally hydrolytically or enzymatically degradable. Instability provided by hydrolytic degradability can be desirable since it permits regulation of the time for which the biological element is protected. Thus, if the polymer is provided with a tissue-specific targeting group, the polymer (or the linkage between the polymer and the biological element) can be designed so that the polymer protects the biological element for as long as it takes for the modified biological element to reach the appropriate location within the target tissue before disintegrating, freeing the biological element to interact with the tissue. Alternatively, the polymer could be designed to disintegrate at a rate yielding optimal kinetics of release of the biological element. Instability provided by enzymatic degradability can be desirable since it permits the polymer (or the linkage between the polymer and the biological element) to be designed for cleavage selectively by chosen enzymes. Such enzymes could be present at the target site, endowing the modified biological element with the possibility of triggered disintegration at the target site, thereby releasing the biological element for interaction with the target tissue. The enzymes may also be intracellular enzymes which can bring about disintegration of the modified biological element in selected cellular compartments of a target cell to enhance the activity of the biological element. Alternatively, enzyme-cleavage sites may be designed to promote disintegration of the modified biological element in response to appropriate biological activity (eg. arrival of an invading or metastatic tumour cell expressing metalloproteinase). In a further variation, enzymes capable of activating the modified biological element may be administered at the appropriate time or site to mediate required disintegration of the modified biological element and subsequent interaction of the biological element with the tissue.

The polymer used to modify the biological element in at least some embodiments is preferably cross-linked such that it forms a hydrogel. The hydrogel is preferably hydrolytically unstable or is degradable by an enzyme, for example matrix metalloproteinases 2 or 9. This is in order that the biological elements are immobilised within the hydrogel and so that the release of the biological elements can be regulated. Thus, according to one preferred feature of the invention, the process of the invention is carried out under conditions likely to promote crosslinking and hydrogel formation (for example high concentrations of reagents with none present in excess) or in the presence of agents such as diamines likely to promote crosslinking. Formation of hydrogels containing modified biological elements would generally be performed using the chemical approaches described in Subr, V., Duncan, R. and Kopecek, J. (1990) "Release of macromolecules and daunomycin from hydrophilic gels containing enzymatically degradable bonds", J. Biomater. Sci. Polymer Edn., 1(4) 261-278.

The number of reactive groups on the polymer is preferably from 0.5 to 10 mol %, more preferably from 1 to 6 mol %, and most preferably from 2 to 5 mol %.

The number of linkages between the polymer and the biological element is preferably three or more, more preferably four or more. The number of linkages may be, for example, 12 or 14. The advantage of having a higher number of linkages is that the polymer modified biological element is more stable.

The two or more linkages between the polymer and the biological element are preferably covalent linkages.

It has been found that normally infective biological elements such as viruses modified in accordance with the invention lose their original infectivity completely. Infectivity may be restored or replaced however in preferred embodiments by coupling a biologically active agent to the polymer. The biologically active agent is optionally coupled to the polymer either before it is combined with the biological element or after. Preferably, in cases where the targeting agent has a plurality of reactive groups it is coupled to the polymer after the polymer has coated the biological element to avoid it interfering with the coupling reaction, but in other cases it may be satisfactory to couple it to the polymer before coating the biological element.

The biologically active agent may be incorporated using the same type of reactive groups as are used to couple the reactive polymer to the biological element, or it may be coupled using different chemistry. In the latter situation a heteromultifunctional reactive polymer (for example containing mixed ONp esters and thiol groups) would be used.

Such biologically active agents are preferably incorporated or coupled onto the surface of polymer-coated biological elements in accordance with the invention to improve targeting, tissue penetration or pharmacokinetics. The biologically active agent may be, for example, a growth factor or cytokine, a sugar, a hormone, a lipid, a phospholipid, a fat, an apolipoprotein, a cell adhesion promoter, an enzyme, a toxin, a peptide, a glycoprotein, a serum protein, a vitamin, a mineral, or an antibody recognising receptor, for example a growth factor receptor, tissue-specific antigen or tumour-associated antigen. Several biologically active agents may be coupled to each polymer-modified biological element, including mixtures. Alternatively, a multi-purpose agent may be linked as the biologically active agent directly to the polymer-modified biological element to permit subsequent attachment of desired molecules.

An antibody is preferably used as the biologically active agent to re-target coated biological elements to a different target site which may comprise, for example, various receptors, different cells, extracellular environments and other proteins. A wide range of different forms of antibody may be used including monoclonal antibodies, polyclonal antibodies, diabodies, chimeric antibodies, humanised antibodies, bi-specific antibodies, camalid antibodies, Fab fragments, Fc fragments.

For use in targeting tumours a suitable biologically active agent is for example an antibody recognizing a cancer associated antigen such as a carcinoembryonic antigen or α-fetoprotein, HER-2 proto-oncogene, prostate specific antigen or MUC-1.

A suitable multi-purpose protein for use as the biologically active agent to act as a generic linker permitting flexibility of application is protein G (this will bind an antibody, allowing surface modification with any IgG class antibody from most species), protein A (which has properties similar to protein G), avidin (which binds biotin with very high affinity allowing the incorporation of any biotin labelled element onto the surface), streptavidin (which has properties similar to avidin), extravidin (which has properties similar to avidin), wheat germ agglutinin (which binds sugars), hexahistidine (which allows for gentle purification on nickel chelate columns), GST (which allows gentle purification by affinity chromatography).

A suitable growth factor or cytokine for use as the biologically active agent is for example Brain derived neurotrophic factor, Cilary neurotrophic factor, b-Endothelial growth factor, Epidermal growth factor (EGF), Fibroblast growth factor Acidic (aFGF), Fibroblast growth factor Basic (bFGF), Granulocyte colony-stimulating factor, Granulocyte macrophage colony-stimulating factor, Growth hormone releasing hormone, Hepatocyte growth factor, Insulin like growth factor-I, Insulin like growth factor-II, Interleukin-1a, Interleukin-1b, Interleukin 2, Interleukin 3, Interleukin 4, Interleukin 5, Interleukin 6, Interleukin 7, Interleukin 8, Interleukin 9, Interleukin 10, Interleukin 11, Interleukin 12, Interleukin 13. Keratinocyte growth factor, Leptin. Liver cell growth Factor, Macrophage Colony stimulating factor, Macrophage inflammatory protein 1a, Macrophage inflammatory protein 1b, Monocyte chemotactic protein 1, 2-methoxyestradiol, b-nerve growth factor, 2.5 s nerve growth factor, 7 s nerve growth factor, Neurotrophin-3, Neurotrophin-4, Platelet derived growth factor AA, Platelet derived growth factor AB, Platelet derived growth factor BB, Sex hormone binding globulin, Stem cell factor. Transforming growth factor-β1, Transforming growth factor-β3, Tumour necrosis factor α, Tumour necrosis factor β, Vascular endothelial growth factor, and Vascular endothelial growth factor C.

A suitable sugar for use as the biologically active agent for incorporation by amino derivatisation in the form of a monosaccharide, disaccharide or polysaccharide is, for example, D-Galactose, D-Mannose, D-Glucose, L-Glucose, L-Fucose, and Lactose.

A hormone which is suitable for use as the biologically active agent is, for example, Adrenomedullin, Adrenocorticotropic hormone, Chorionic gonadotropic hormone, Corticosterone, Estradiol, Estriol, Folicle stimulating hormone, Gastrin 1, Glucagon, Gonadotrophin, Growth hormone, Hydrocortisone, Insulin, Leptin, Melanocyte stimulating hormone, Melatonin, Oxytocin, Parathyroid hormone, Prolactin, Progesterone, Secretin, Thrombopoetin, Thyrotropin, Thyroid stimulating hormone, and Vasopressin.

A suitable lipid, fat or phospholipid for use as the biologically active agent for targeting the polymer coated biological element or for providing stealth-like properties is, for example, Cholesterol, Glycerol, a Glycolipid, a long chain fatty acid, particularly an unsaturated fatty acid e.g. Oleic acid, Platelet activating factor, Sphingomylin, Phosphatidyl choline, or Phosphatidyl serine.

A suitable cell adhesion promoter for use as the biologically active agent can be provided by, for example, Fibronectin, Laminin. Thrombospondin, Vitronectin, polycations, integrins or by oligopeptide sequences binding integrins or tetraspan proteins.

A suitable apoliproprotein for use as the biologically active agent that may also provide stealth-like properties is, for example, a high density lipoprotein or a low density lipoprotein, or a component thereof.

A suitable enzyme for use as the biologically active agent, for example, to promote mobility of the coated biological element through a particular environment is an enzyme capable of degrading the extracellular matrix (for example a gelatinase, e.g. matrix metallo proteases type 1 to 11, or a hyaluronidase), an enzyme capable of degrading nucleic acids (for example Deoxyribonuclease I, Deoxyribonuclease II, Nuclease, Ribonuclease A), an enzyme capable of degrading protein (for example Carboxypeptidase, plasmin Cathepsins, Endoproteinase, Pepsin, Proteinase K, Thrombin, Trypsin, Tissue type plasminogen activator or Urokinase type plasminogen activator), an enzyme allowing rapid detection (for example Luciferase, Peroxidase, b-galactosidase), or other useful enzymes such as Amylase, Endoglycosidase, Endo-b-galactosidase, Galactosidases, Heparinase, HIV reverse transcriptase, b-hydroxybutyrate dehydrogenase, Insulin receptor kinase, Lysozyme, Neuraminidase, Nitric oxide synthase, Protein disulphide isomerase.

A suitable toxin for use as the biologically active agent to bind a receptor or to interact with cell membranes is, for example, Cholera toxin B subunit, Crotoxin B subunit, Dendrotoxin, Ricin B chain.

A suitable peptide for use as the biologically active agent may be provided by, for example, transferrin, Green/blue/yellow fluorescent protein, Adrenomedullin, Amyloid peptide, Angiotensin I, Angiotensin II, Arg-Gly-Asp, Atriopeptin, Endothelin, Fibrinopeptide A, Fibrinopeptide B, Galanin, Gastrin, Glutathione, Laminin, Neuropeptide, Asn-Gly-Arg, Peptides containing integrin binding motifs, targeting peptides identified using phage libraries, peptides containing nuclear localisation sequences and peptides containing mitochondrial homing sequences.

A suitable serum protein for use as the biologically active agent is, for example, Albumin, Complement proteins, Transferrin, Fibrinogen, or Plasminogen.

A suitable vitamin or mineral for use as a biologically active agent is, for example, Vitamin $B_{12}$, Vitamin $B_{16}$ or folic acid.

It will thus be seen that a polymer modified biological element in accordance with the present invention can be synthesised so as to be targeted to a highly specific set of cells, e.g. tumour cells. At the same time, however, it has been found that polymer modified biological elements in accordance with the present invention are not generally rendered inactive by neutralising antibodies. This is believed to be because the modified biological element is shielded by the polymer. The shielding of the biological element by the polymer has been found to have other potential advantages, including increased shelf life and better resistance to low pH. Also it may be possible to purify such biological elements using more aggressive technology than that which is feasible with existing unmodified biological elements.

Optionally the polymer can be coupled to a radioisotope in order to allow the detection of the biological element e.g. in a biological environment.

Bacterial biological elements used in carrying out the invention may include, for example, bacteria used in experimental gene therapy (e.g. *salmonella*), bacteria or baculovirus used as a biological pesticide (e.g. nuclear polydedrosis virus NPD, nonocclude virus NV, granulosis virus or *bacillus thuringiensis*), a bacteria strain useful for degrading oil sludges/spills or a genetically modified version thereof (e.g. *enterobacteriaceae, anitratum, pseudomonas, micrococcus, comamonas, zanthomonas, achromobacter* or *vidrio-aeromonas*), a bacterial strain responsible for reducing sulphur to $H_2S$ in oil (e.g. *petrotoga mobilis, petrotoga miotherma, desulfotomaculum nigrificans, desulphovibrio*) or a bacterial strain capable of oxidising sulphur from oil (e.g. *rhodococcus* sp. Strain ECRD-1).

In principle any known virus may be used in the present invention as the biological element. The virus is preferably a recombinant genetically engineered virus. The recombinant virus optionally contains a transgene. It will be understood that the term "transgene" is used herein to denote a nucleic acid which is not native to a virus. For example a transgene could encode a biologically functional protein or peptide, an antisense molecule, or a marker molecule. The virus is either an RNA or DNA virus and is optionally from one of the following families and groups: Adenoviridae; Alfamoviruses; Bromoviridae; Alphacryptoviruses; Partitiviridae; Baculoviridae; Badnaviruses; Betacryptoviruses; Partitiviridae; Bigeminiviruses; Geminiviridae; Birnaviridae; Bromoviruses; Bromoviridae; Bymoviruses; Potyviridae; Bunyaviridae; Caliciviridae; Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus $\Phi$6 phage group; Cystoviridae; Cytorhabdoviruses; Rhabdoviridae; Group Carnation ringspot; Dianthovirus virus group; Group Broad bean wilt; Enamoviruse; Fabavirus virus group; Fijiviruses: Reoviridae; Filoviridae; Flaviviridae; Furovirus group; Group Gemini virus; Group Giardiavirus; Hepadnaviridae; Herpesviridae; Hordeivirus virus group; Hybrigeminiviruses: Geminivirida; Idaeoviruses; Ilarvirus virus group; Inoviridae; Ipomoviruses: Potyviridae; Iriodoviridae; Levivridae; Lipothrixviridae; Luteovirus group; Machlomoviruses; Macluraviruses; Marafivirus virus group; Maize chlorotic dwarf virus group; icroviridae; Monogeminiviruses: Geminiviridae; Myoviridae; Nanaviruses; Necrovirus group; Nepovirus virus group; Nodaviridae; Nucleorhabdoviruses: Rhabdoviridae; Orthomyxoviridae; Oryzaviruses: Reoviridae; Ourmiaviruses; Papovaviridae; Paramyxoviridae; Parsnip yellow fleck virus group; Partitiviridae; Parvoviridae including adeno-associated viruses; Pea enation mosaic virus group; Phycodnaviridae; Phytoreoviruses: Reoviridae; Picornaviridae; Plasmarviridae; Podoviridae; Polydnaviridae; Potexvirus group; Potyvirus; Poxviridae; Reoviridae; Retroviridae; Rhabdoviridae; Group Rhizidiovirus; Rymoviruses: Potyviridae; Satellite RNAs; Satelliviruses; Sequiviruses: Sequiviridae; Sobemoviruses; Siphoviridae; Sobemovirus group; SSVI-Type Phages; Tectiriviridae; Tenuivirus; Tetravirirdae; Group Tobamovirus; Group Tobravirus; Togaviridae; Group Tombusvirus; Tospoviruses: Bunyaviridae; Group Torovirus; Totiviridae; Tymoviruses; Group Tymovirus; Plant virus satellites; Umbraviruses; Unassigned potyviruses: Potyviridae; Unassigned rhabdoviruses: Rhabdoviridae; Varicosaviruses; Waikaviruses: Sequiviridae; Ungrouped viruses.

A particularly preferred virus for use in the invention is a retrovirus, adenovirus, adenoassociated virus, baculovirus, herpesvirus, papovavirus or poxvirus. Adenovirus is especially preferred, including non-human adenovirus such as avian adenovirus CELO.

A component of a biological element which is suitable for use as the biological element may be provided by, for example, a viral core or a provirus (from e.g. pox viruses). An example of a viral core is an adenovirus core which is preparable by the method disclosed in Russell, W. C., M., K., Skehel, J. J. (1972). "The preparation and properties of adenovirus cores" Journal of General Virology 11, 35-46 and modifications thereto.

A phage which is suitable for use as the biological element is for example one from one of the following families: Cyanophages, Lambdoid phages, Inovirus, Leviviridae, Styloviridae, Microviridae, Plectrovirus, Plasmaviridae, Corticoviridae, Satellite bacteriophage, Myoviridae, Podoviridae, T-even phages. An example of a particular phage is MV-L3, P1, P2, P22, $\Phi$29, SP01, T4, T7, MV-L2, PM2, F1, MV-L51, $\Phi$X174, $\Phi$6, MS2, M13, Q$\beta$, tectiviridae (eg. PRD1).

Figure 3:
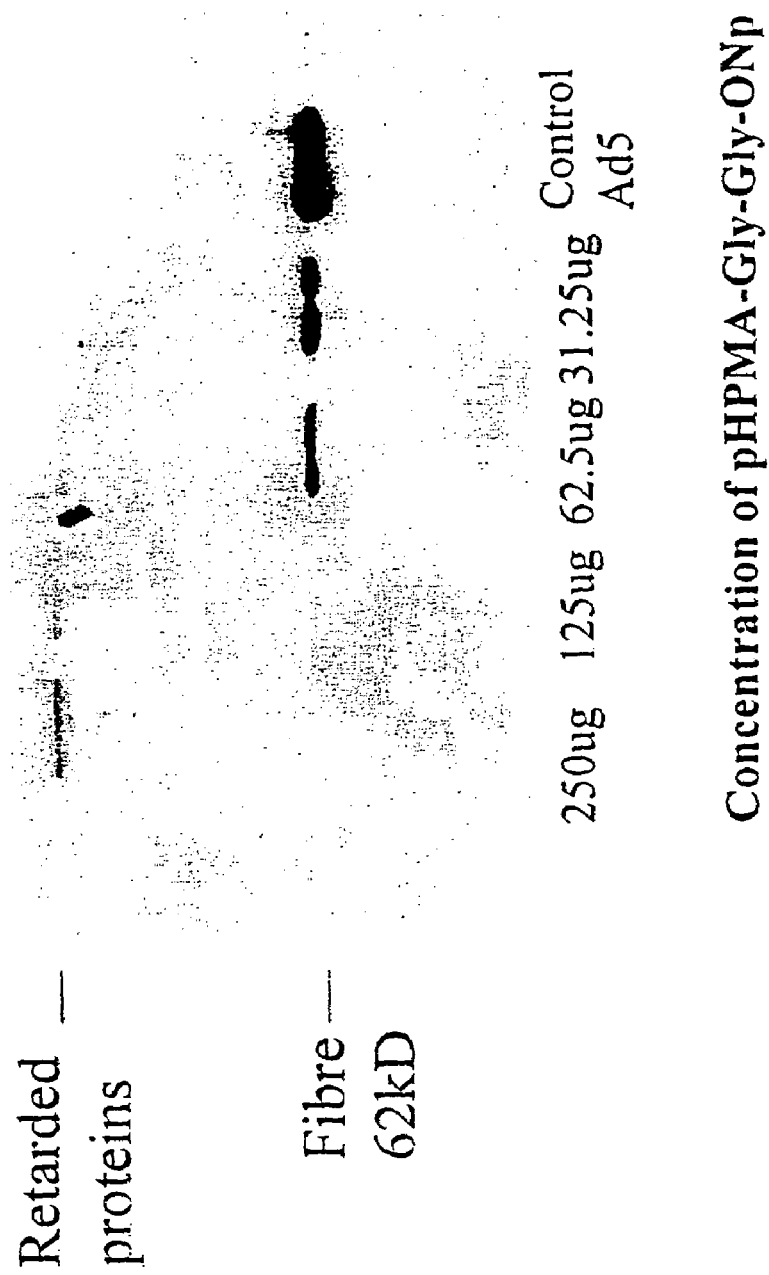

A fungus which is suitable for use as the biological element is for example one from family Basidiomycetes (which make basidiospores, which include classes such as Gasteromycetes, hymenomycetes, urediniomycetes, ustilaginomycetes), *Beauveria, Metarrhizium, Entomophthora* or *Coelomomyces*. A spore which is suitable for use as the biological element is a basidiospore, actinomyceres, arthrobacter, microbacterium, clostridium, Rhodococcus, Thermomonospora or *Aspergillus fumigatus.*

A further example of a bacterium which is suitable for use as the biological element is one selected from the group consisting of *Rickettsiella popiliae, Bacillus popiliae, B. thuringiensis* (including its subspecies *israelensis, kurstaki* and *B. sphaericus*), *B. lentimorbus, B. sphaericus, Clostridium malacosome, Pseudomonas aeruginosa* and *Xenorhabdus nematophilus.*

The process according to the invention is preferably carried out at a pH greater than 7. More preferably the process is carried out at a pH from 7.4 to 8.2, most preferably about pH 8. Generally speaking the process is faster at higher pH values but the rate of hydrolysis of the polymer is faster too. A suitable buffer is generally used in the process; suitable buffers include phosphate, borate, carbonate or HEPES buffers. The temperature of the process is preferably below room temperature, more preferably in the range from 4 to 10° C. The process is preferably carried out with mixing. Using pHPMA reactive polymer in carrying out virus-coating reactions in accordance with the invention, a preferred concentration range for the polymer will be 2-20 mg/ml, with a most preferred concentration generally being in the range of 5-10 mg/ml.

The compositions according to the invention can be suitable for in vitro use or for use in plants or animals. Where the composition is for use in an animal, especially a mammalian animal, the carrier is preferably a pharmaceutically acceptable additive, diluent or excipient.

BRIEF DESCRIPTION OF THE DRAWINGS

In the accompanying drawings

FIG. 1 shows fluorescamine measurement of free amino groups on adenovirus particles following surface modification with a synthetic polymer. Reaction of adenovirus with reactive polymers decreases the number of free amino groups on the surface of the virus. Here the virus is reacted with varying amounts of pHPMA-Gly-Gly-ONp and the residual level of amino groups is determined using the fluorescamine assay (see Example 8 below).

FIG. 2 illustrates the spectrophotometric determination of a typical reaction between polymers and adenoviruses. Reaction of reactive polymers with adenovirus can be monitored spectrophotometrically, either by production of free 4-nitrophenol or by loss of reactive ester. Here the reaction at pH values 7.4, 7.8, 8.0 and 8.5 is monitored by production of free 4-nitrophenol (A410 nm), and is compared in each case with a virus-free control. The top line in each pair (suffixed "v") shows the rate of reaction in the presence of virus, indicating the rate of reaction with virus plus the rate of hydrolysis, while the lower line in each pair simply records the rate of hydrolysis alone, at each pH value (see Example 9 below).

FIG. 3 illustrates a Western blot showing that reaction of polymer with adenovirus leads to modification of fibre protein. Further details are given in Example 10. This Western blot compares the signal determined for adenovirus fibre protein by Western blotting of viruses treated with increasing amounts of pHPMA-Gly-Gly-ONp. It can be seen that fibre runs normally when low amounts of polymer are used, but higher amounts of polymer leads to a change in mobility and possibly a change in efficiency of detection for the fibre protein. This indicates covalent modification of the fibre by the polymer, and possibly implicates crosslinking.

FIG. 4 illustrates a reduction in cytotoxicity of adenovirus following surface modification using a multivalent polymer, pHPMA-Gly-Phe-Leu-Gly-ONp. (A) shows wild type A549 cells, growing healthily. (B) shows the cells infected with wild type Ad5 virus, indicating significant cytopathic effect. (C) shows cells treated with mono-pEGylated wild type Ad5 virus, indicating that pEGylation does not remove the cytopathic effect. (D) shows cells treated with pHPMA-Gly-Phe-Leu-Gly-ONp modified wild type Ad5, showing complete abolition of the cytopathic effect, with cells growing normally.

Figure 5:
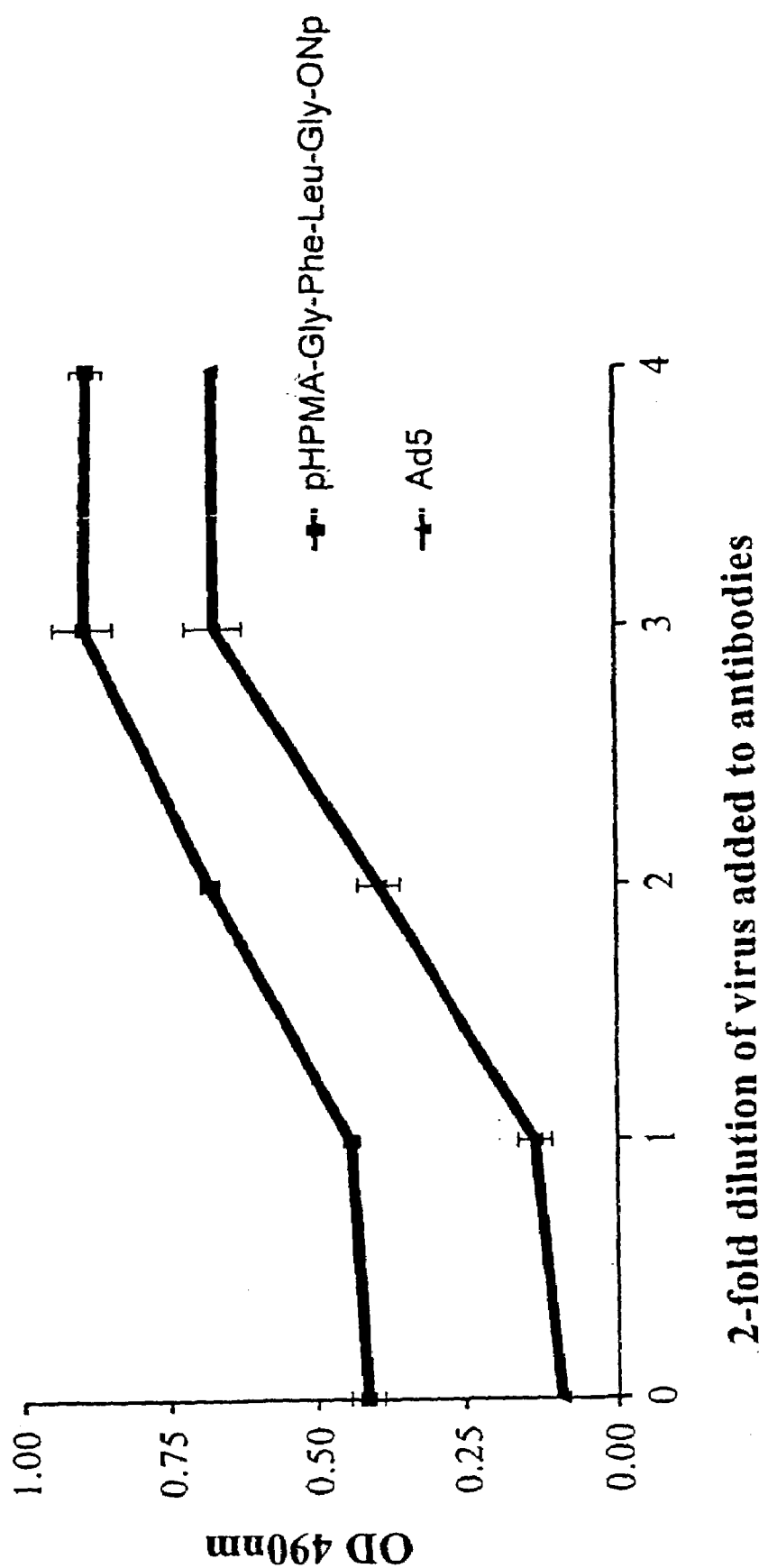

FIG. 5 illustrates reduced antibody binding of polymer-coated adenovirus as determined using competition ELISA.

Solutions containing anti-adenovirus antibodies were pre-incubated with wild type Ad5 virus or polymer-modified Ad 5v virus, at a range of concentrations of virus. Residual antibodies were then determined using an ELISA system with wild type Ad5 as the ligand. It can be seen that many more free antibodies remained when solutions were pre-depleted with coated virus than when solutions were pre-depleted with wild type virus. This indicates protection of antibody binding by the presence of the polymer coat.

Figure 6:
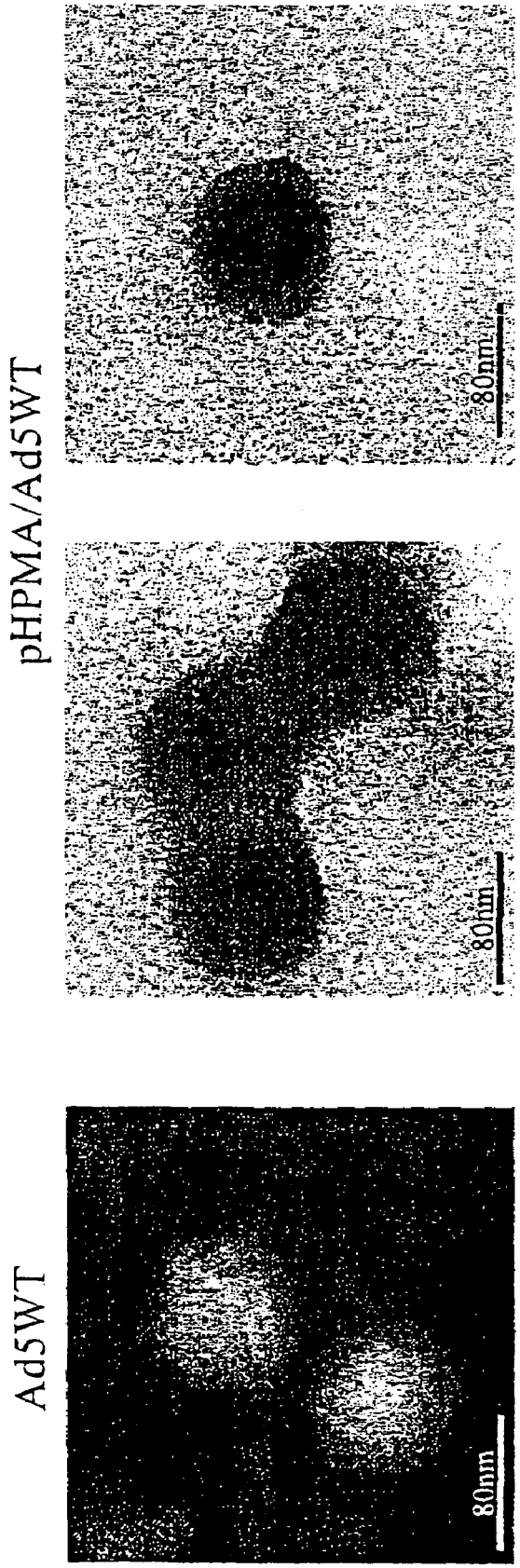

FIG. 6 illustrates some physical characteristics of pHPMA coated adenorius. Wild type Ad5 and polymer-coated Ad5 were visualised by Transmission Electron Microscopy (TEM; magnification ×100 000). Samples were stained with 2% phosphotungstic acid, pH 7.0. Observation by TEM showed the particle size for both Ad5WT and coated virus to be 80 nm in diameter; Ad5WT was negatively stained whereas due to the presence of pHPMA, the coated virus was positively stained. Measurement by photon correlation spectroscopy (PCS) showed that the particle size for Ad5WT was the same as that measured by TEM at 80 nm. However, when the particle size of pHPMA coated virus was determined by PCS it was shown to be almost 20% greater than that of Ad5WT at 94 nm. Further description is given in Example 13.

Figure 7:
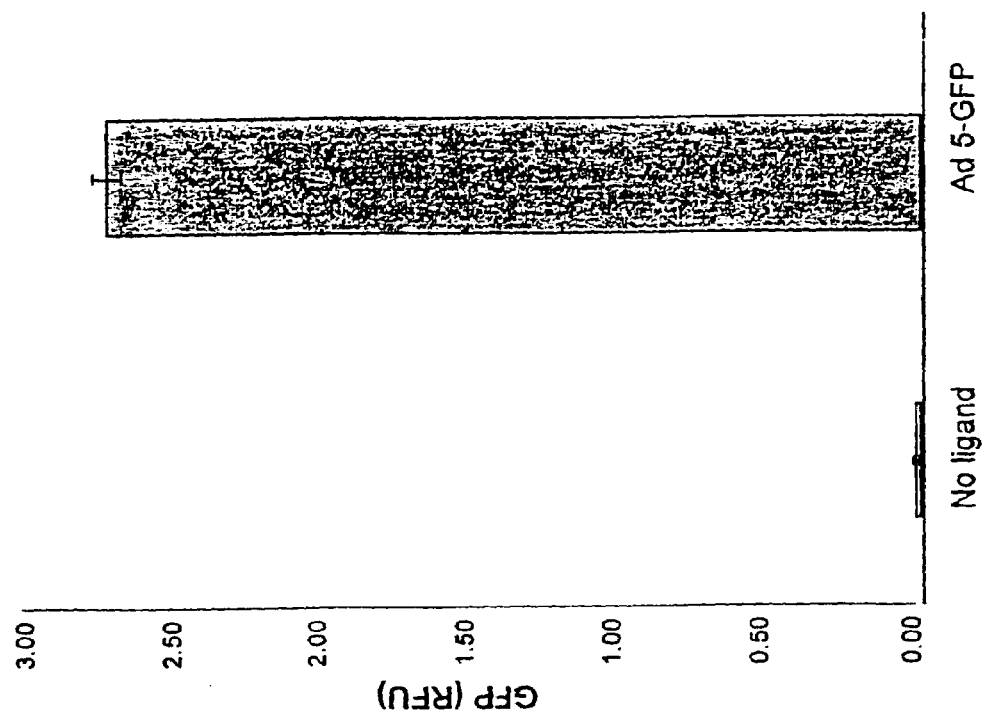

FIG. 7 illustrates the reduction of infectivity of Ad5-GFP in A549 cells following reaction with pHPMA-Gly-Gly-ONp. Ad5-GFP (unmodified parental virus) was treated with reactive pHPMA-Gly-Gly-ONp as described in Example 13 below. A549 cells were exposed to viruses for 48 h and the level of green fluorescence protein (GFP) expression was determined using fluorescence. Coating the virus with pHPMA mediated a significant fall in GFP expression, reflecting a major inhibition of virus infectivity. The reference to "ligand" refers to ligand attached to the polymer modified virus.

Figure 8:
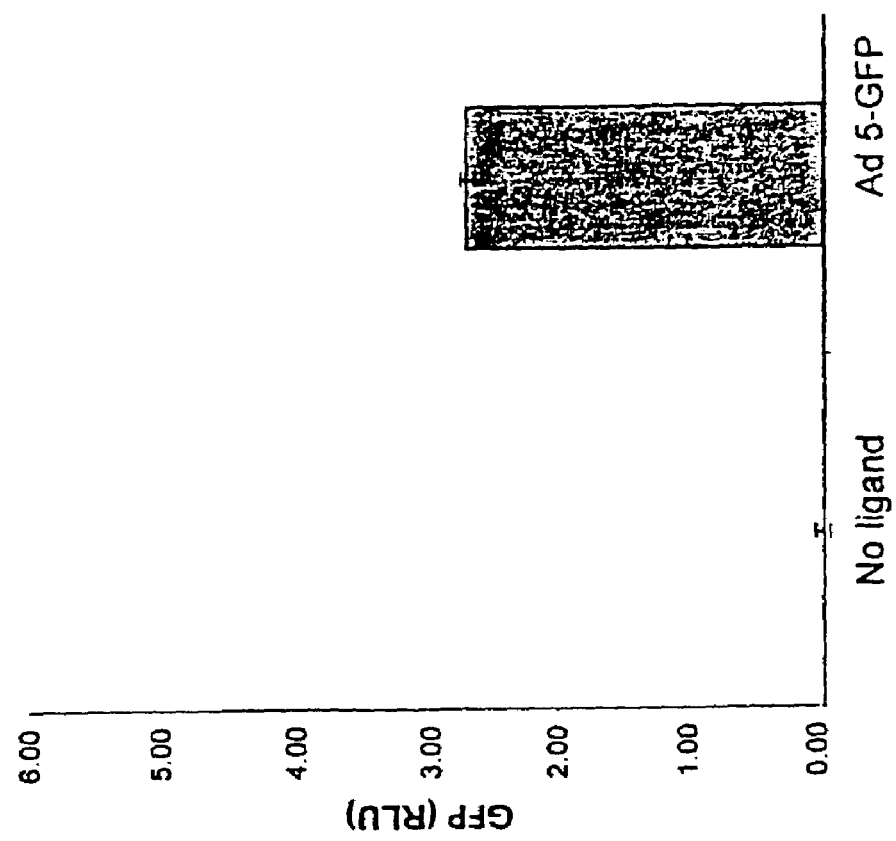

FIG. 8 illustrates a reduction of infectivity of Ad5-GFP in human umbilical vein endothelial (HUVE) cells following reaction with pHPMA-Gly-Gly-ONp. Ad5-GFP was treated with reactive pHPMA-Gly-Gly-ONp as described in the text (see Example 14). HUVE cells were exposed to viruses for 48 h and the level of GFP expression was determined using fluorescence. Coating the virus with pHPMA mediated a significant fall in GFP expression, reflecting a major inhibition of virus infectivity. Again, the reference to "ligand" refers to ligand attached to the polymer modified virus.

Figure 9:
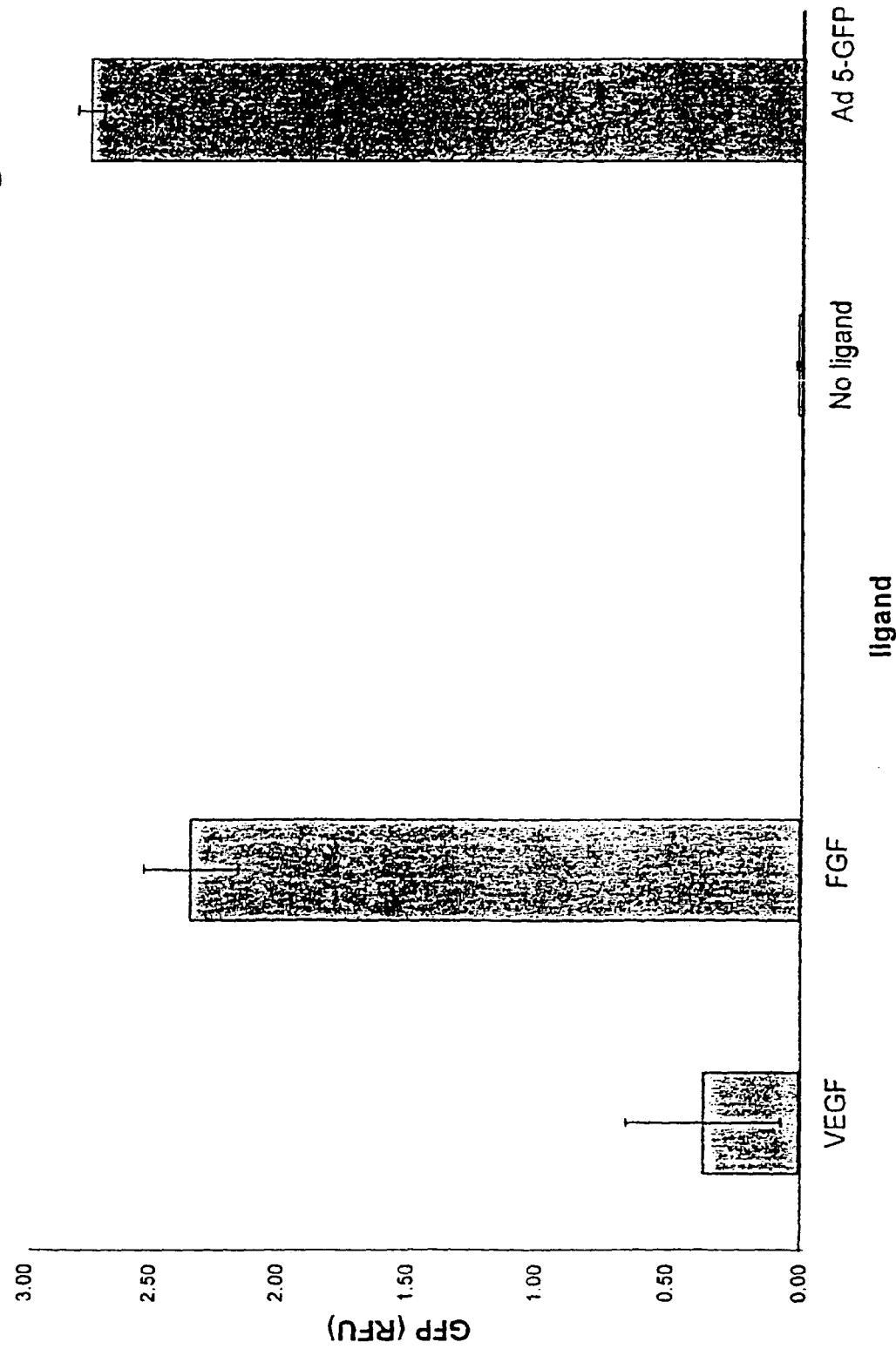

FIG. 9 shows restoration of infectivity in A549 cells by retargeting polymer-coated viruses with growth factors bFGF or VEGF. Ad5 viruses were reacted with pHPMA-Gly-Phe-Leu-Gly-ONp and then retargeted by reaction with bFGF or VEGF. Viruses were then incubated with A549 cells, and cellular expression of GFP was measured after 48 h. bFGF restored both the uptake and the infection inhibited by the polymer-coating, while VEGF produced only a weak restoration of GFP expression. This may reflect the presence a relatively high level of bFGF receptors on these cells, and a low level of VEGF receptors.

Figure 10:
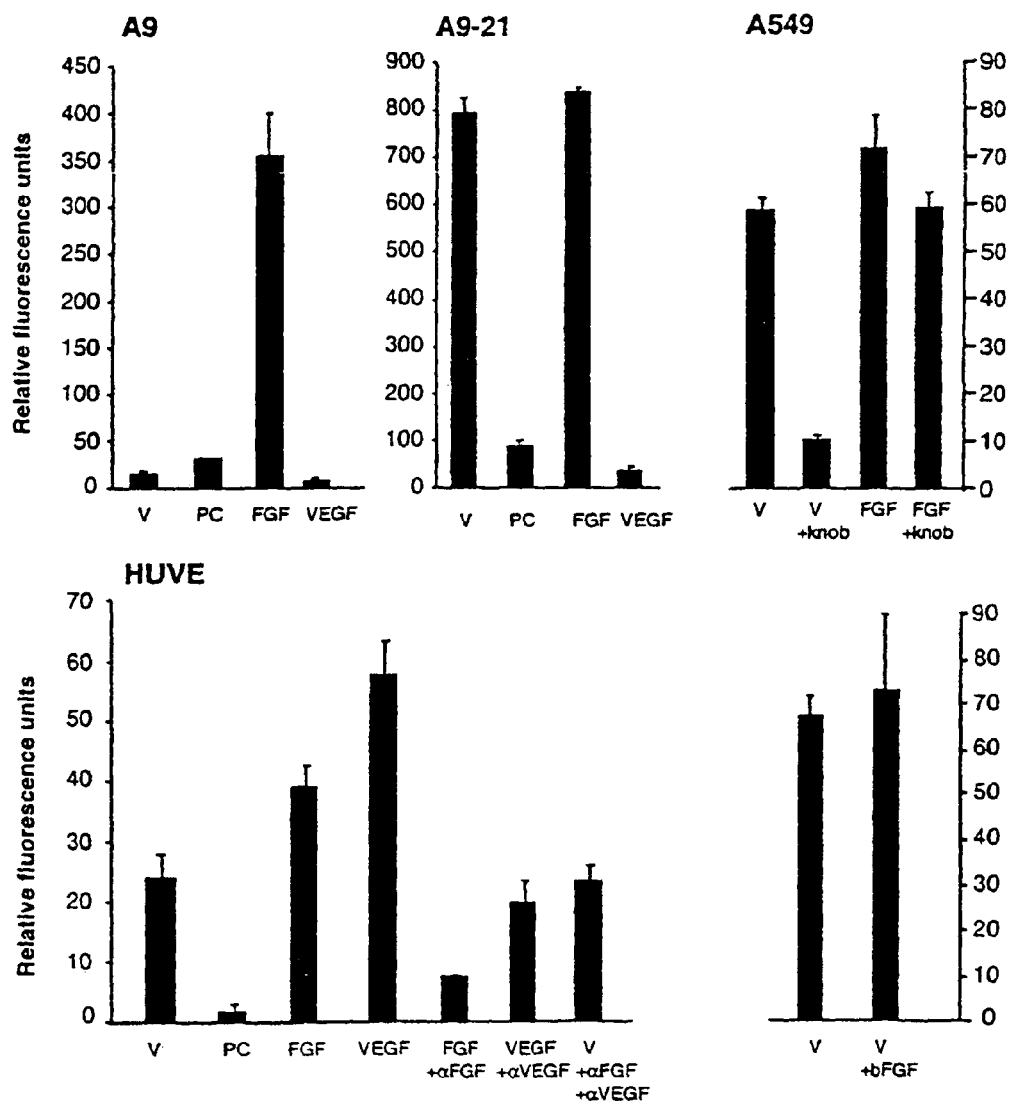

FIG. 10 shows an analysis of restoration of infectivity in A9, A9-21, A549 and human vein umbilical endothelial (HUVE) cells by retargeting polymer-coated viruses with bFGF or VEGF. Ad5 viruses were reacted with pHPMA-Gly-Gly-ONp and then retargeted by reaction with bFGF or VEGF. Viruses were then incubated with cells, and cellular expression of GFP was measured after 48 h. Presence of both bFGF or VEGF restored infectivity to HUVE cells, although VEGF was more effective, probably reflecting a high level of VEGF receptors expressed on these cells. Specificity of infection was demonstrated by antagonising infection of HUVE cells using retargeted viruses and applying appropriate anti-ligand antibodies (anti-bFGF and anti-VEGF antibodies). Infection of A549 could not be antagonised by adding excess fibre knob domain, however, indicating that CAR binding does not play a role in the infectivity of the retargeted polymer-coated viruses.

Figure 11:
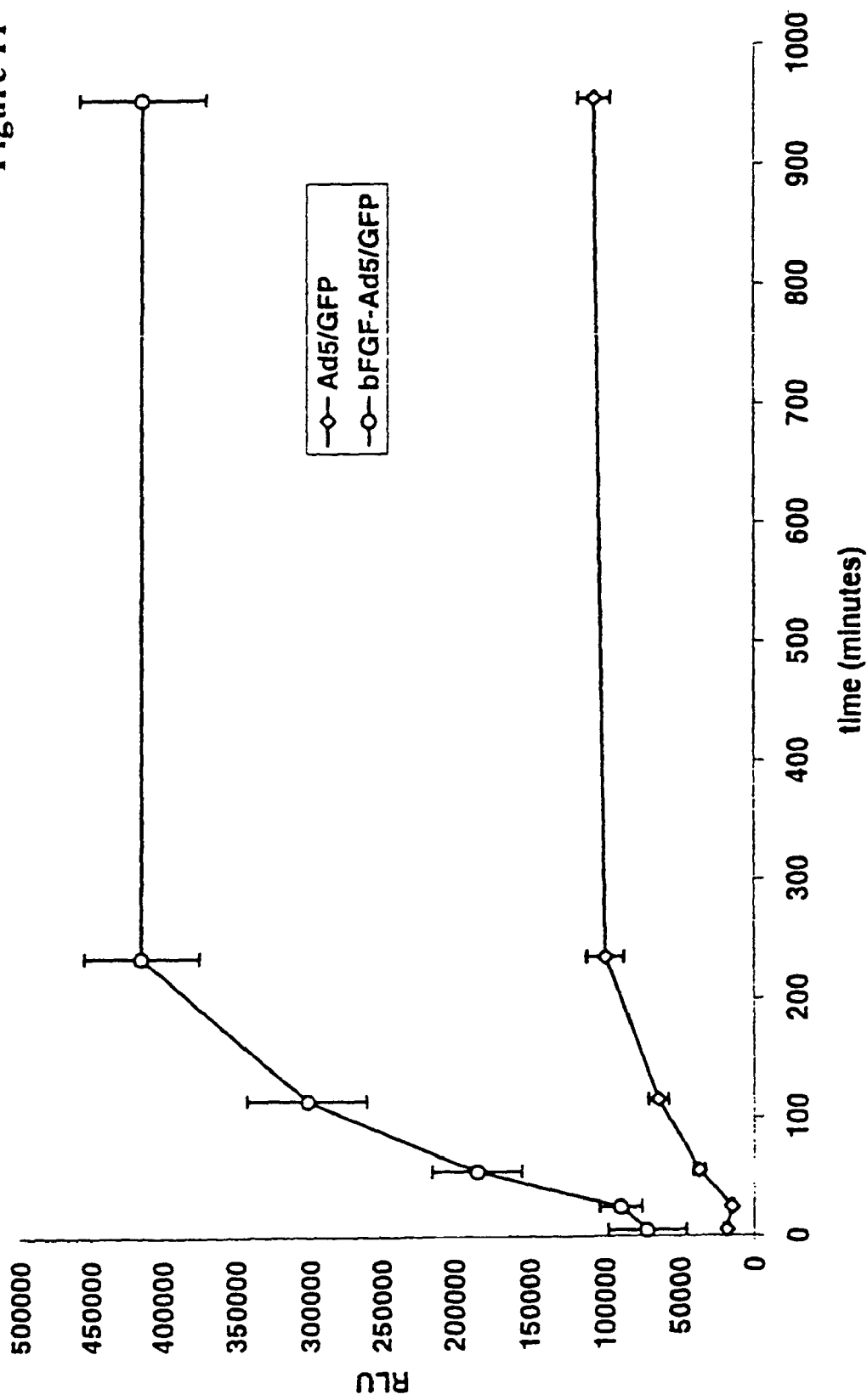

FIG. 11 shows the effect when a bFGF-retargeted polymer-coated virus was used to infect the primary ovarian carcinoma "polyclonal" cell line YSK19. Significant levels of gene expression were achieved, considerably greater than with the unmodified virus. Infections were performed for varying lengths of time, and it can be seen that both agents reached their maximum infective level after only 4 h incubation.

Figure 12:
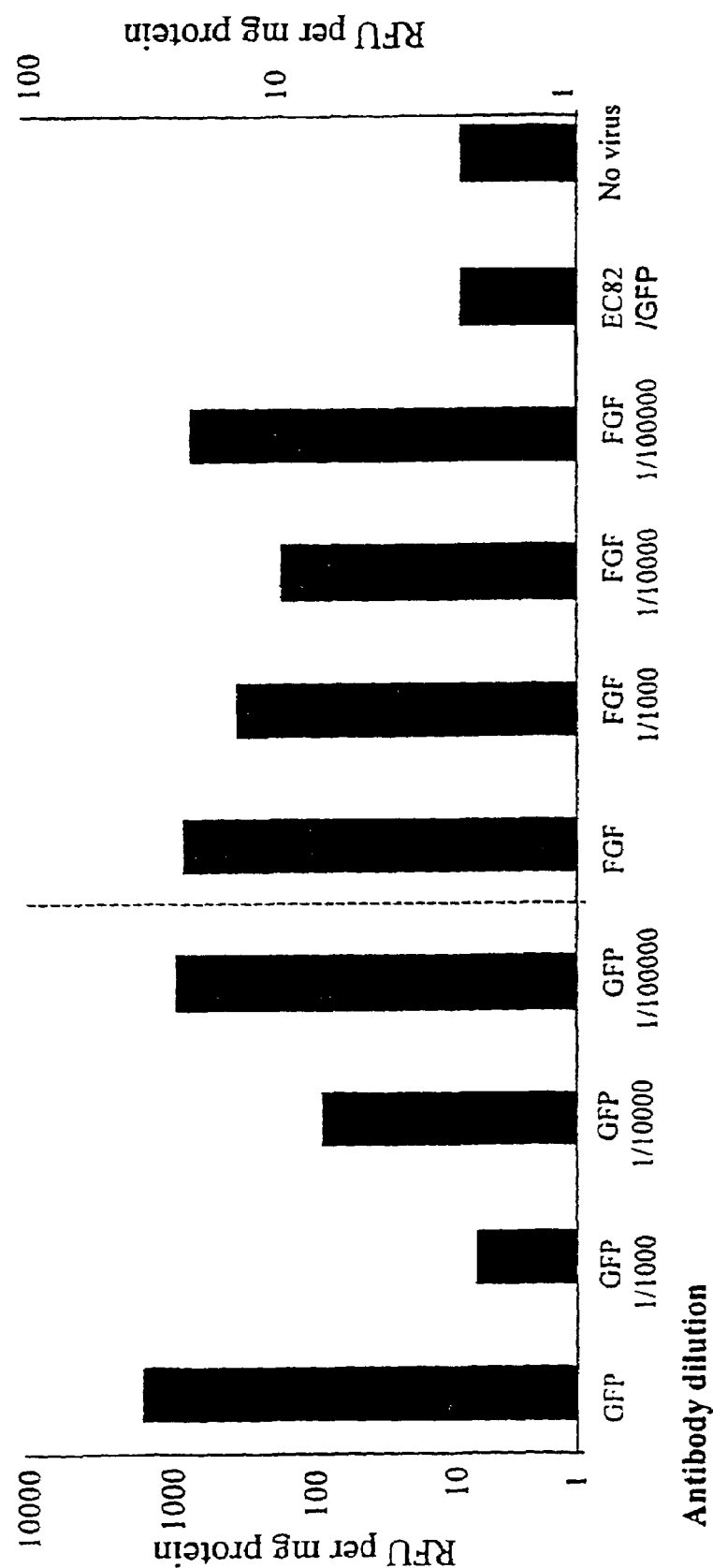

FIG. 12 shows an evaluation of the effects of neutralising antibodies to inhibit infection using Ad5-GFP or Ad5-GFP modified with pHPMA-Gly-Phe-Leu-Gly-ONp (referred to as EC82 in the drawing). A549 cells were infected with $10^4$ particles/cell Ad5-GFP, or pHPMA-modified Ad5-GFP or bFGF-retargeted pHPMA-modified Ad5-GFP (prepared as described in Example 15) in the presence of various dilutions of rabbit anti-Ad5 serum. At 5 days post-infection GFP fluorescence was measured in the cells, and protein concentration determined. Infectivity of coated virus was restored by addition of bFGF. Neutralisation was reduced by less than 20% with retargeted coated virus compared with a reduction of 99.2% for Ad5-GFP alone.

Figure 13:
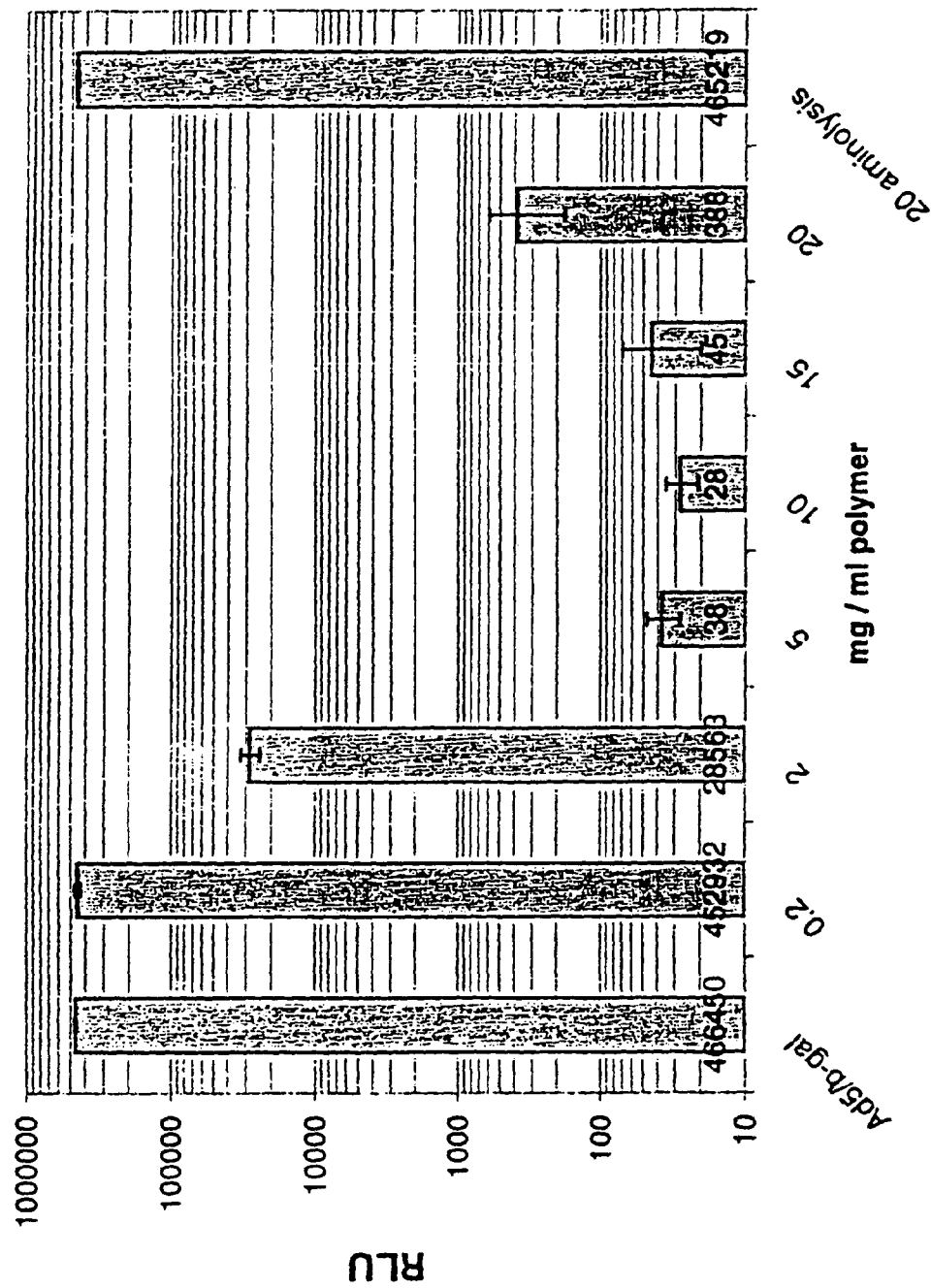

FIG. 13 shows the influence of the concentration of reactive polymer on the residual infective activity of polymer-modified adenovirus.

MORE DETAILED DESCRIPTION OF
PREPARATION METHODS AND EXAMPLES

The following examples and descriptions of stages in synthetic routes for preparation of polymer coated viruses for use as nucleic acid delivery vehicles, and other biological elements constructed in accordance with the invention, serve to further illustrate the present invention and disclose additional important features thereof. They should not, however, be construed in any way as a limitation thereof.

Unless otherwise stated, molecular weight values quoted for polymers are intended to represent weight average values. In the Examples the virus concentrations are given as the number of viral particles per ml. This is generally much greater than the corresponding number of infectious units.

In the first example (EXAMPLE 1), the manner of preparation is described of an adenovirus formed with a protective hydrophilic polymer coating in accordance with the invention.

Example 1

Preparation of a Polymer-Modified Virus Having a Coating of Hydrophilic Polymer Formed by Polymeric Precursors Based on N-2-hydroxypropylmethacrylamide (HPMA) and Reactive Esters This example relates to the formation of a coated virus made up of adenovirus and a so-called polymeric precursor composed of HPMA copolymerised with a methacryloylated-oligopeptide(Glycine-Phenylalanine-Leucine-Glycine) para-nitrophenyl ester.

Such methacrylic polymeric precursors provide the hydrophilic polymer material. They will generally have a molecular weight of about 20,000 Da and contain from 4-10 mol % of oligopeptide side chains bearing activated ester groups (-ONp). The oligopeptide acts as a spacer and may be varied in size, but the tetrapeptide Gly-Phe-Leu-Gly (SEQ ID NO:1) represents one preferred form which is designed for biodegradation by lysosomal cathepsin enzymes (thiol proteinases). A typical structure is shown below:

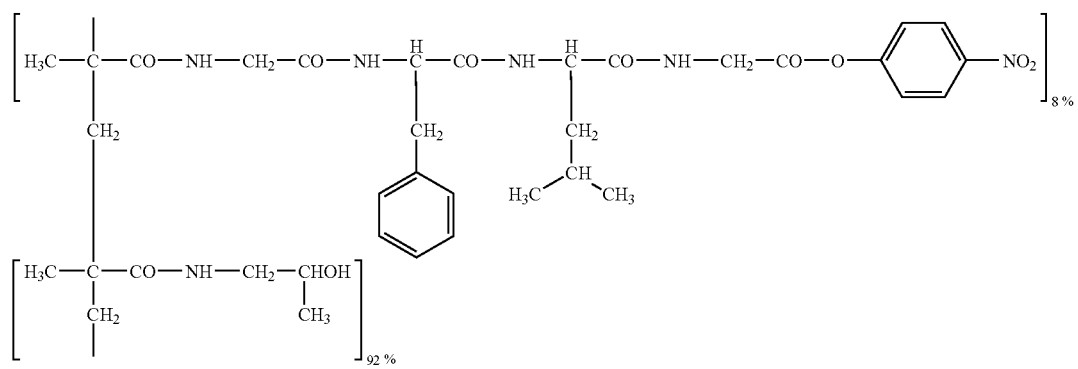

Ulbrich, K. et al, "Polymeric Conjugates of Drugs and Antibodies for Site-Specific Drug-Delivery" *Macromolecular Symposia*, (1996), 103, pp. 177-192. See also EP-A-0187547 of which the content is incorporated herein by reference.

The preparation of hydrophilic poly(HPMA) polymers having side chains bearing reactive p-nitrophenyl esters or reactive p-nitrophenoxy groups is more particularly described in Examples 3 and 4 of WO 98/19710.

It is incidentally also possible for constructing the hydrophilic polymer to use polymeric precursors of HPMA copolymerised with N-methacryloylated oligopeptides in which the peptide side chains terminate in carboxyl groups instead of p-nitrophenyl ester groups, prepared as described in EP-A-0187547. In the presence of suitable catalysts (again see EP-A-0187547) the carboxyl groups will bind to primary amino groups on the viruses to be coated, as with nitrophenyl esters. However, an additional possibility also arises in that the carboxyl groups may bind to reactive alcohol groups in the virus, forming ester groups. In that event such ester groups may be subsequently broken down through acid-catalysed or hydrolytic degradation.

Adenovirus (25 μg, equivalent to $8.6\times10^{10}$ viral particles) was incubated in 100 μl phosphate buffered saline(PBS)/glycerol (10% vol/vol) containing 50 mM HEPES buffer pH 7.4 at 6° C. The hydrophilic polymer (polymeric precursor) bearing reactive ester groups was dissolved in water and added to the mixture with gentle mixing (final concentration 2.5 mg/ml). It is important that the solution does not contain nucleophilic groups such as reactive amines (eg. Tris buffer) which could react with the ester groups. It is also important that the solution should not become too alkaline (eg. pH not >8.2) as this will promote unwanted hydrolysis of the activated ester groups. It is also important that the pH of the virus solution does not fall below 7.0 as this will begin to inactivate the adenovirus.

The reaction between the —ONp ester groups and the primary amino functions of the virus was monitored spectrophotometrically, either by measuring decreasing concentration of the esters (274 nm) or by monitoring appearance of free 4-nitrophenol (404-410 nm). After 1 h aminoethanol (0.1%, vol/vol) was added to terminate the reaction. In some instances, for application of viruses at high concentrations, free 4-nitrophenol is subsequently removed by filtration or dialysis before application to cells.

Optimal reaction conditions include gentle mixing (but not vortexing) either in HEPES buffer, borate solution or in Preparation of methacrylic polymeric precursors as referred to above generally involves a step of copolymerisation of HPMA with the p-nitrophenyl ester of the N-methacryloylated peptide concerned, and in the "polymeric precursor" so formed the terminal p-nitrophenoxy groups of the peptide side-chains provide convenient leaving groups for subsequent addition reactions with reactive amino or other functional groups of the viruses. The synthesis of p-nitrophenyl esters of N-methacryloylated oligopeptides and their copolymers with HPMA is well documented in the literature, especially in articles or papers relating to synthetic polymer drug delivery agents, as for example P. Rejmanova et al "Aminolyses of Monomeric and Polymeric 4-Nitrophenyl Esters of N-Methacryloylamino Acids", (1977), *Makromol. Chem.* 178, 2159-2168, Subr. V, et al, "Polymers Containing Enzymatically Degradable Bonds", (1992), *Journal of Controlled Release,* 18, No. 2, pp. 123-132 and water at pH 7.0-8.2, temperature of 4-10° C. and a maximal virus concentration of $10^{13}$ particles/ml to minimise crosslinking.

In some instances the pH may be gradually raised during the reaction, either by addition of sodium hydroxide or a higher pH buffer, up to about pH 8.0. This promotes reactivity of the primary amino groups, but must be regulated carefully as it also accelerates the rate of ester hydrolysis.

The reaction may be terminated either by raising the pH to 8.5, promoting rapid ester hydrolysis, or preferably by addition of low molecular weight reactive amines, e.g. aminoethanol, aminopropanol or ethylenediamine.

It has also been found that the coated viruses so formed are relatively stable and easy to handle, and they can be purified by column chromatography (eg. Sepharose 4B-CL) or by density gradient centrifugation.

Synthesis of the reactive hydrophilic polymer used in the above example which contains tetrapeptide-paranitrophenyl esters, has already been referred to. Careful selection of the reactive hydrophilic coating polymer can significantly affect the properties of the resulting coated viruses. For example, use of polymers having simple oligopeptide-nitrophenol ester reactive side chains leads to aminolytic reaction with uncharged amino groups of the viruses with release of p-nitrophenol, but there is also a significant component of hydrolysis. The hydrolytic product is a free carboxylic acid at the terminal amino acid, and hence such coated viruses are often found to possess strongly negative surface charges (eg. zeta potential of −25 mV). Alternative chemistry, for example using carbonate esters of paranitrophenol yield the same products on aminolysis, with release of carbon dioxide, but produce hydroxyl groups following hydrolysis. The measured zeta potential of the resulting coated viruses is generally very close to zero.

Several other reactive hydrophilic polymers can be used to achieve surface-coating of viruses. These include reactive esters based on other polymer backbones, such as poly-N5-(2-hydroxyethyl)-L-glutamine (pHEG), or reactive polymers containing backbones composed primarily of blocks of poly(ethylene glycol) joined end-to-end by oligopeptide or other biodegradable sequences bearing pendant reactive esters. Careful selection of the structure of these molecules can tailor them for degradation by specific enzymes, in specific locations, or for hydrolytic or acid-catalysed hydrolytic degradation. The synthesis of some of these materials is described in later examples, and they make particularly effective agents for surface modification of viruses using the same protocol as described above. Reactive hydrophilic polymer material based on poly-N-(2-hydroxyethyl-L-glutamine) (pHEG), containing reactive ONp carbonate esters with no amino acid spacer, can be produced by reaction of pHEG with chloroformate and is known to be readily biodegradable.

Coated viruses formed with a net strong negative surface charge are subject to rapid scavenging by phagocytic cells, notably Kupffer cells, following intravenous administration. Coated viruses bearing net positive charges are prone to accumulation in capillary beds, notably the pulmonary capillaries. Accordingly, the best surface charge for achieving prolonged plasma circulation is neutral or slightly negative.

As will be appreciated, other bioactive molecules, such as targeting groups or additional shielding molecules, may be attached to the hydrophilic polymer precursor. In an example described below (EXAMPLE 2), the targeting agent transferrin has been incorporated by simple aminolysis or following oxidation of its carbohydrate component.

Example 2

Construction of Transferrin-Targeted Coated Viruses Using Aminolysis

E1-disabled adenovirus (25 µg, equivalent to $8.6 \times 10^{10}$ viral particles) encoding the β-galactosidase reporter gene under the control of the cytomegalovirus immediate-early promoter in E1 was incubated in 100 µl phosphate buffered saline(PBS)/glycerol (10% vol/vol) containing 50 mM HEPES buffer pH 7.4 at 6° C. Reactive hydrophilic polymer (pHPMA bearing 8 mol % Gly-Phe-Leu-Gly-4-nitrophenol esters, as from Example 1) was added (final concentration 2.5 mg/ml). The reaction was allowed to proceed for 1 h before addition of holotransferrin (20 µg) and the reaction was then allowed to continue for a further 1 h. At that time the reaction was ended by addition of aminoethanol (0.1% vol/vol), the viruses were allowed to stand for a further 30 min and then purified by dialysis.

As an alternative the above reaction may be performed in an automatic titration apparatus (e.g. a pH-Stat from Radiometer) maintained at 6° C. and programmed to maintain the pH at 7.4

The coated viruses were then incubated in medium containing 2% foetal calf serum with transferrin receptor-positive K562 cells ($10^4$ cells/well in 94-well plates), final virus concentration $10^8$ particles/well. After 72 h cells were lysed in phosphate buffer (100 mM, pH 7.2 containing Triton X-100 (0.1%, vol/vol)) prior to measurement of β-galactosidnase reporter gene expression using a commercial Galactolight™ luminescence assay kit. Transferrin-targeted coated viruses were found to mediate significantly higher gene expression than non-targeted polymer-coated viruses, and this transfection activity could be inhibited by the addition of excess competing free transferrin. When incubated with transferrin receptor-negative 293 cells, however, these transferrin-targeted complexes gave no transfection activity.

Despite this demonstration of transferrin-targeted gene expression using coated viruses, the result was rather unexpected since it was previously unclear whether the coated viruses would be able to leave the endosome/lysosome system and enter the cytoplasm. This example demonstrates the ability of coated viruses to function effectively following their entry into cells in transferrin-mediated internalisation.

Example 3

Construction of Transferrin Targeted Coated Viruses Using Carbohydrate Oxidation Adenoviruses were coated with a reactive hydrophilic polymer as described above. In contrast to Example 2, however, no transferrin was used and the coating reaction was terminated by the addition of a 20-fold molar excess of diaminoethylene. This resulted in the incorporation of amino groups onto the surface of the coated viruses via the remaining unreacted ONp ester groups. The amino group-bearing coated viruses were purified from free diamine and polymer by gel filtration on Sepharose 4B-CL with distilled water as eluent.

For the oxidation of the transferrin carbohydrate chain, 10 mg transferrin (0.13 µmol) was dissolved in 0.45 ml of sodium acetate buffer (pH 5.0, 30 mM) and chilled to 0° C. Freshly dissolved sodium periodate (50 µl of a 10 mg/ml solution) was added and the reaction was performed for 90 min at 0° C. in the dark. The oxidised transferrin was purified by gel filtration on prepacked PD10 columns (Pharmacia) and the presence of aldehyde groups was demonstrated using the anisaldehyde test. The oxidised transferrin was kept at pH 5.0 to prevent autoreaction.

For linkage of the oxidised transferrin to the amino function-bearing coated viruses the pH was adjusted to 7.4 and an appropriate amount of oxidised transferrin was added to purified coated complexes. The mixture was left for 1-2 hrs to permit formation of Schiff's base type covalent linkages. The Schiff's bases were subsequently stabilised by reduction for a minimum of 1 hr using an excess of cyanoborohydride. Finally the viruses were purified from unincorporated transferrin and cyanoborohydride and sterilised by gel filtration on Sepharose 4B-CL or equivalent with PBS pH 7.4 as eluent.

Biological activity was demonstrated as described above.

Example 4

Construction of Transferrin Targeted Polymer-Coated Adenoviruses Using a Heterobifunctional Crosslinker This procedure involved production of polymer-coated viruses bearing SH groups and their conjugation with SH-reactive transferrin molecules.

Virus preparations were produced by propagating adenovirus in permissive cell lines. Cysteamine (2-aminoethane thiol) was reacted with pHPMA-based reactive coating polymer at different ratios (from 2 to 25% equivalent to the reactive esters) prior to addition to the viruses. This reaction was carried out in a pH-Stat (Radiometer) at pH 7.4 and 16° C., as follows:

An appropriate amount of the precursor form of the hydrophilic coating material (for example 400 μg/ml of a pHPMA-based copolymer with 8 mol % activated ester group) was dissolved in water and the desired amount of cysteamine was added. The reaction of the polymer precursor with cysteamine was started by raising the pH to 7.4. The reaction is very rapid and is essentially complete after 3 min. The modified polymer precursor was stored at pH 6.0 to prevent unwanted hydrolysis.

An equal volume of adenovirus was then added to the modified polymer precursor. The reaction of the coating material with the amino groups of the virus was initiated by increasing the pH to 7.4, and allowed to proceed for 2 hrs. Unreacted ONp ester groups were then reacted with an excess of aminopropanol.

Sulphide-reactive transferrin was prepared as follows: Transferrin was dissolved in water at 25 ng/ml. Between 1-2 molar-equivalents of succinimidopyridyldithiopropionate (SPDP) was added (for 1 ml of 25 mg/ml transferrin, around 20 μl of a 10 mg/ml SPDP solution would be used). The mixture was left for 1 hr at room temperature before being subjected to gel filtration using a PD10 column.

The sulphide-reactive pyridyldithiopropionate-transferrin (PDP-Tf) was then reacted onto sulphide-bearing coated viruses. This was achieved by adding an appropriate amount of the PDP-Tf to a solution of coated viruses prepared as described above under neutral conditions. The exchange reaction was allowed to proceed overnight.

All reactions were carried out in an oxygen-free atmosphere using degassed solutions to prevent formation of disulphide bonds by the coating polymer, potentially leading to the formation of aggregates. For the same reason a molar excess of sulphide-reactive transferrin over sulphide groups of the coating material was used. After completion of all reactions, the viruses were purified from non-incorporated materials and reaction by-products and sterilised by aseptic gel filtration on Sepharose 4B-CL or other suitable matrices. Phosphate buffered saline was used as the eluent. Biological activity was demonstrated as described above.

Example 5

Reaction of the Virus Complex with pEG-SH

Adenoviruses were incubated and surface-modified using a multivalent polymer bearing reactive esters and free thiol groups as described in Example 4. The coated virus was mixed under argon with a solution of 100 mg pEG-SH in 3 ml phosphate buffer, pH 7.4 (oxygen-free). The reaction was carried out at room temperature for 4 hours. The pEG-containing complex produced was examined by agarose gel electrophoresis, atomic force microscopy, and photon correlation spectroscopy. The grafting of pEG (5 mol %) via disulfide bonds was confirmed by UV spectroscopy (absorption at 412 nm) after reaction with DTT, followed by quantitative determination of the pEG-SH released using 5,5'-dithiobis(2-nitrobenzoic acid) (DTNB).

Example 6

Coating of Viruses with Reactive Hydrophilic Polymers which are Biodegradable in the Polymer Backbone.

In this example adenoviruses were stabilised by surface modification using a hydrophilic polymer bearing pendant reactive esters, namely a pEG-peptide-ONp repeating polymer. This hydrophilic polymer was formed from alternating blocks of poly(ethylene glycol) and tripeptides, designed to introduce proteolytic degradability into the polymer backbone, and was prepared as described in parts 11.1 and 11.2 of Example 11 of WO 98/19710.

The reactive pEG-peptide-ONp repeating polymer (dissolved in DMSO) was added to viruses in PBS/glycerol (10%) containing HEPES buffer (50 mM) (pH 7.4) to a final concentration of 200 μg/ml. The solution went gradually yellow as free paranitrophenol was released. Infectivity of viruses was determined by titreing against A549 cells, and was found to be decreased by the presence of the polymer coating.

Example 7

Surface Modification of Biological Elements Bearing Aldehyde Groups Using Polymers Derivatised with Hydrazide Groups.

Attachment of surface coating polymers through bonds which are acid unstable and labile at endosomal pH is one important aspect of this invention. There are several chemical strategies suitable for this purpose, but one is exemplified here.

Synthesis of Hydrazide-Modified Hydrophilic Polymer (a) $1^{st}$ stage: Coupling of pHPMA-ONp with Succinic Acid t-butyl-oxycarbonylhydrazide 0.2 g pHPMA-ONp was aminolysed with ethylene diamine at pH 8.0 in HEPES buffer. The material was dialysed into water and mixed with succinic acid t-butyloxycarbonylhydrazide (20.64 mg, 0.156 mmol). The pH of the solution was adjusted to 5.0 with HCl. Subsequently, 300 mg of 1-ethyl-3-(3-dimethylaminopropyl)-carbodiimide (EDC) (1.56 mmol) in water was added to this solution. The pH was maintained at 5.0 with HCl during the reaction. After stirring overnight, the solution was dialysed for 48 h against water. The polymer was collected by freeze drying. The degree of substitution was determined by means of $^1$H-NMR and was 4%.

(b) $2^{nd}$ stage: Removal of the t-butyloxycarbonyl (BOC) Protecting Group 0.2 g of this modified pHPMA derivative (above) was dissolved in 10 ml trifluoroacetic acid. The mixture was stirred for 1 h and the solvent was evaporated. The residue was dissolved in water and further dialysed for 48 h. The polymer was collected by freeze-drying. The degree of substitution was determined by means of $^1$H-NMR and was found to be 3.8%.

(c) $3^{rd}$ stage: Grafting of *Aspergillus fumigatus* Spores with the Hydrazide-Modified pHPMA.

Spores of *Aspergillus* (50 μg) were incubated with the hydrazide-modified pHPMA (200 μg) in citrate buffer at pH 5.0 and stirred for 2 h. The amount of pHPMA grafted onto the spores was calculated following determination of spore-associated aldehyde groups using Benedict's reagent.

Example 8

Determination of pHPMA-Gly-Gly-ONp Modification of Wild Type Adenovirus Type 5 (wt Ad5) Particles by Fluorescamine Assay.

To quantify the extent of amino group modification of wt Ad5 surface proteins, pHPMA-Gly-Gly-ONp treated adenovirus was compared to un-modified Ad5 using amino reactive fluorescamine.

Figure 1:
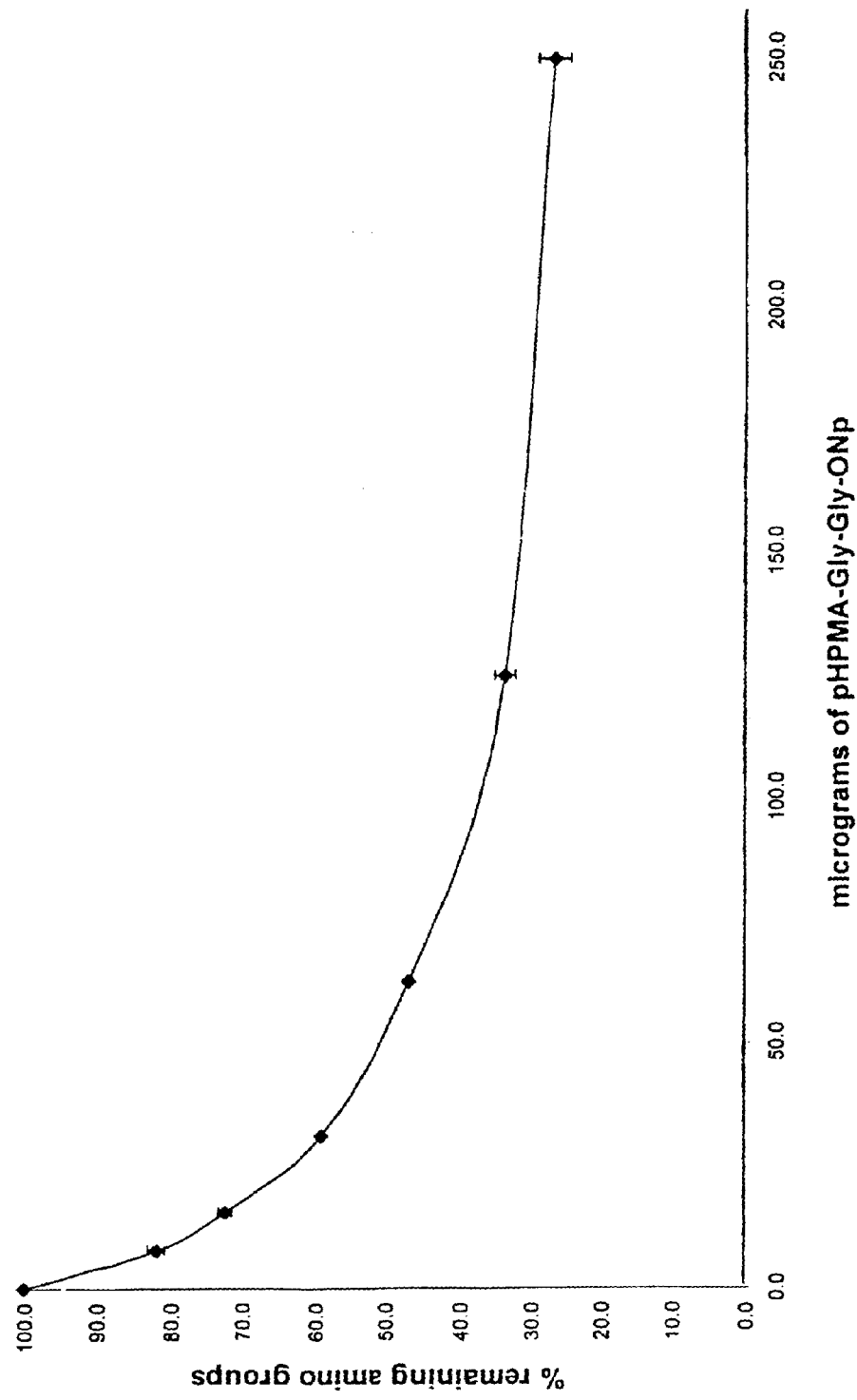

25 μg ($8.6\times10^{10}$) of wt Ad5 particles in 100 μl of PBS glycerol (10%) and 50 mM HEPES pH 7.4 were treated with 0-250 μg of pHPMA-Gly-Gly-ONp for 1 hour on ice. 1 mg of this preparation was diluted in 375 μl of PBS glycerol (10%) and made up to 500 μl with acetone containing 100 μg/ml fluorescamine. After 5 minutes reaction with fluorescamine, fluorescence was measured at 392ex:480em in a quartz cuvette. Results were expressed as percentage of amino groups lost compared with untreated virus, and the background signal for un-reacted fluorescamine on its own was removed (FIG. 1).

Example 9

Measurement of pHPMA-Gly-Gly-ONp Reaction with wt Ad5 by Release of 4-nitrophenol.

The reaction of pHMPA with amino groups or by hydrolysis yields free 4-nitrophenol which can be measured at 404 nm or 410 nm. Alternatively loss of the reactive ester can be monitored at 274 nm.

Figure 2:
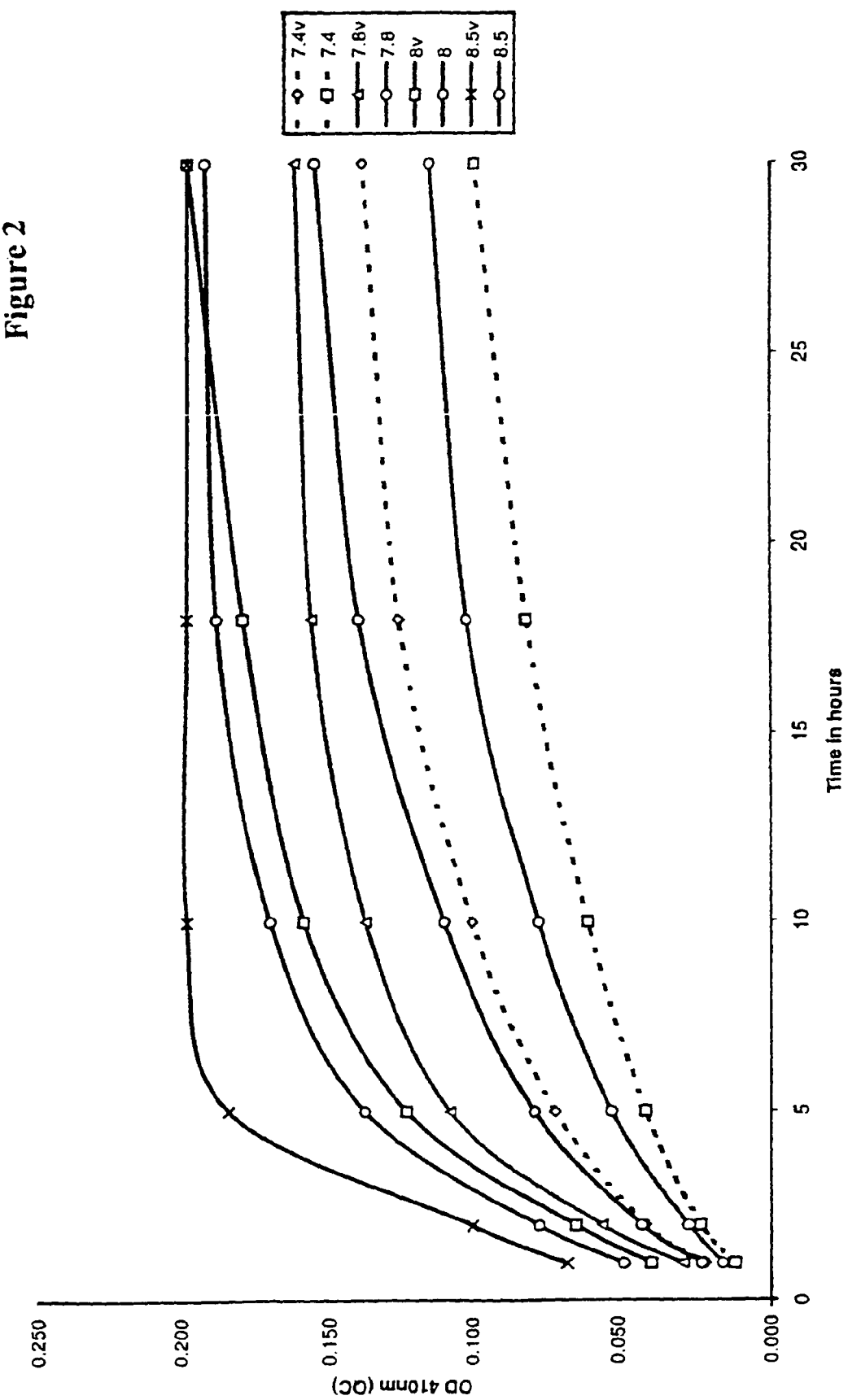

250 μg/ml of wt Ad5 in PBS glycerol (10%) and 50 mM HEPES pH 7.4-8.5 were treated with 5 mg/ml of pHPMA-Gly-Gly-ONp, and production of free paranitrophenol was measured in a 1 ml quartz cuvette as a function of time at different pH values. The rate of reaction was compared to pHPMA-Gly-Gly-ONp without virus to get a background level of hydrolysis (FIG. 2). The presence of the virus stimulated significantly faster reaction, indicating the formation of covalent bonds between the virus and the polymer. The reaction is most efficient at pH 7.8-8.0 when the aminolysis:hydrolysis ratio is highest.

Example 10

Western Blot Demonstration of wt Ad5 Fiber Modification by pHPMA-Gly-Gly-ONp.

To determine changes in mobility imposed on viral proteins following reaction with pHPMA-Gly-Gly-ONp, coated viruses were analysed by SDS-PAGE and transferred to nitrocellulose paper for detection with antibodies (in this case anti-fiber antibody).

25 μg ($8.6\times10^{10}$) of wt Ad5 particles in 100 μl of PBS glycerol (10%) and 50 mM HEPES pH 7.4 were treated with 0-250 μg of pHPMA-Gly-Gly-ONp for 1 hour on ice. Subsequently, 0.1% amino ethanol was added to complete the reaction with any spare ester groups. 2 μg ($6.9\times10^9$) wt Ad5 particles were denatured and separated on a 12% SDS PAGE gel for 2 hours at 200V. Proteins were then transferred to nitrocellulose and electrophoresed for 45 minutes at 10V. The nitrocellulose membrane was then blocked with 5% Marvel in 0.1% Tween PBS for 1 hour at room temperature before being probed with 1/1000 dilution of guinea pig anti Ad5 fiber antibody in 0.1% Tween PBS for 1 hour. The membrane was washed 3 times for 10 minutes in 0.1% Tween PBS and exposed to 1/10000 dilution of anti guinea pig peroxidase conjugate (SIGMA) in 0.1% PBS Tween for 1 hour. The results (FIG. 3) showed that mobility is reduced providing a sufficient concentration of polymer is used.

Example 11

Reduction of Cytopathic Effect of wt Ad5 by Modification with pHPMA-Gly-Gly-ONp

Wild type Ad5 will infect many cell types with high efficiency and this event causes an obvious change in cell morphology called a cytopathic effect (CPE). Modification of wt Ad5 with a multivalent hydrophilic polymer, in this case pHPMA-Gly-Gly-ONp, reduces its ability to produce a cytopathic effect as observed by the following protocol.

25 μg ($8.6\times10^{10}$) of wt Ad5 particles in 100 μl of PBS glycerol (10%) and 50 mM HEPES pH 7.4 were treated with 0-250 μg of pHPMA-Gly-Gly-ONp for 1 hour on ice. Subsequently, 0.1% amino ethanol was added to complete the reaction with any spare ester groups. 0.25 μg ($8.6\times10^8$) of this preparation was diluted in 500 μl of DMEM 10% foetal calf serum, supplemented with 2 mM glutamine and incubated with a monolayer of A549 cells ($10^5$) in a 24 well plate. Images of the cell monolayers were then captured with a digital camera after 48 hours (FIG. 4). It should be noted that $8.6\times10^8$ pHPMA-Gly-Gly-ONp treated adenovirus particles were unable to cause a CPE although this is 860 times the value that is normally required for adenovirus to produce a 100% CPE.

Example 12

Reduction of Antibody Interaction with pHPMA-Gly-Phe-Leu-Gly-ONp Treated Adenovirus.

The ability of adenovirus to infect target cells can be compromised by the presence of neutralising antibodies. In the preparation herein described, which is unlikely to be optimum, a substantial loss in antibody binding was observed.

20 ng of heat treated wt Ad5 (56° C. for 30 mins) was added in 100 μl to wells of a 96 well plate for 2 hours in PBS glycerol (10%). Meanwhile, serial two-fold dilutions of wt Ad5 or pHPMA-Gly-Phe-Leu-Gly-ONp treated wt Ad5

(maximum concentration 5 µg/ml) were pre-incubated with rabbit anti Ad5 serum (1/1000) in PBS 0.1% Tween for 1 hour. The pre-incubated mixture was then added to the washed 96-well plate (3×PBS 0.1% Tween, 3×PBS) coated with wt Ad5 for two hours to bind any remaining antibodies. The plate was then washed again (3×PBS 0.1% Tween, 3×PBS) and a secondary anti rabbit peroxidase conjugate (1/10000) was added in PBS 0.1% Tween for a further 2 hours. The colour reaction was initiated by addition of OPD reagent dissolved in 0.1M citrate buffer for 30 minutes, the reaction was then stopped with 50 µl of 4M $H_2SO_4$, and read at 490 nm. The results (FIG. 5) demonstrated reduced antibody binding by the polymer modified adenovirus.

Example 13

Loss of Ad5-GFP Ability to Express Reporter Gene in A549 Cells after Treatment with pHPMA-Gly-Gly-ONp and Characterisation of Coated Viruses by Electron Microscopy.

Coating adenovirus with a multifunctional hydrophilic polymer, in this case pHPMA-Gly-Gly-ONp, prevents gene expression as recorded by the green fluorescence protein (GFP) reporter gene in A549 cells.

25 µg ($8.6 \times 10^{10}$) of Ad5-GFP particles in 100 µl of PBS glycerol (10%) and 50 mM HEPES pH 7.4 were treated with 0-250 µg of pHPMA-Gly-Gly-ONp for 1 hour on ice. Subsequently 0.1% amino ethanol was added to complete the reaction with any spare ester groups. Coated and non-coated viruses were visualised using transmission electron microscopy. Changes in affinity for phosphotungstic acid between uncoated and coated viruses indicated the presence of a polymer surface coat, and coated viruses showed a very slightly larger diameter, consistent with the presence of a surface coating of the polymer. There was also an indication of a small amount of aggregation following polymer-coating, with some viruses appearing as dimers or trimers (FIG. 6). $10^7$-$10^9$ particles of this preparation were added to $10^4$ A549 cells in a 96 well plate in DMEM containing 2% foetal calf serum, supplemented with 2 mM Glutamine. After 72 hours cells were lysed using 100 mM potassium phosphate buffer with 0.2% Triton pH 7.2 and fluorescence was determined using a 96-well fluorimeter. The result (FIG. 7) demonstrated complete loss of infective activity after the coating procedure.

Example 14

Loss of Ad5-GFP Ability to Express Reporter Gene in HUVE Cells after Treatment with pHPMA-Gly-Gly-ONp Coating adenovirus with a multifunctional hydrophilic polymer, in this case pHPMA-Gly-Gly-ONp, also prevents gene expression as recorded by the green fluorescence protein reporter gene in HUVE cells.

25 µg ($8.6 \times 10^{10}$) of Ad5-GFP particles in 100 µl of PBS glycerol (10%) and 50 mM HEPES pH 7.4 were treated with 0-250 µg of pHPMA-Gly-Gly-ONp for 1 hour on ice. After which, 0.1% amino ethanol was added to complete the reaction with any spare ester groups. $10^7$-$10^9$ particles of this preparation was added to $10^4$ HUVE cells in a 96 well plate in DMEM containing 2% foetal calf serum, supplemented with 2 mM Glutamine. After 72 hours the cells were lysed using 100 mM potassium phosphate buffer with 0.2% triton pH 7.2 and fluorescence was determined using a 96-well fluorimeter. The result (FIG. 8) again demonstrated complete loss of infective activity after the coating procedure.

Example 15

Restoration of Gene Expression in A549, HUVE, A9, SKOV3 and YSK19 Cells Following Retargeting of pHPMA-Gly-Gly-ONp-Modified Viruses As shown, above coating adenovirus with a multifunctional hydrophilic polymer, in this case pHPMA-Gly-Gly-ONp, prevents gene expression as recorded by the green fluorescence protein reporter gene (Examples 13 and 14). FIG. 9 demonstrates that the complete loss of infective activity observed following application of the coating procedure can be reversed by incorporation of bFGF as targeting agent. bFGF-retargeted polymer-coated adenovirus shows levels of gene expression comparable with unmodified parental Ad5-GFP. In contrast, VEGF-retargeted coated virus shows little activity, probably reflecting the low number of VEGF receptors present on these cells as previously mentioned.

In establishing this feature, 25 µg ($8.6 \times 10^{10}$) of Ad5-GFP particles in 100 µl of PBS/glycerol (10%) and 50 mM HEPES pH 7.4 were treated with 250 µg of pHPMA-Gly-Phe-Leu-Gly-ONp for 1 hour on ice. 10 µg of bFGF or VEGF was then added for a further 1 hour. Subsequently, 0.1% amino ethanol was added to complete the reaction with any spare ester groups. A549 cells were seeded into 96-well plates ($10^4$ cells/well) and samples were infected with E1-deleted Adenovirus 5 encoding the gene for green fluorescence protein (Adgfp$_{AE1}$), polymer-coated Adgfp$_{AE1}$ (pc-Adgfp$_{AE1}$), bFGF-retargeted pc-Adgfp$_{AE1}$ (bFGF-pc-Adgfp$_{AE1}$) or VEGF-retargeted pc-Adgfp$_{AE1}$ in phenol red-free DMEM/2% foetal calf serum (FCS). At 48 h post infection (pi) cells were examined for gfp fluorescence.

The same procedure was applied to HUVE cells. FIG. 10 shows that the abolition of infectivity measured using HUVE cells following polymer-coating (PC) of Ad5-GFP can also be reversed by incorporation of bFGF as targeting ligand. In these cells, retargeting with bFGF yields an infectivity greater than that observed using the parental non-coated virus (V). VEGF also acts as an effective retargeting agent in these cells, consistent with the high level of VEGF receptors expressed on HUVE cells, and mediates levels of infectivity still greater than those achieved using the non-coated virus.

Selectivity and CAR independence of infection was demonstrated by preincubating (1 h, 37° C.) cells with adenovirus fibre knob domain (50 µg/ml; A549 cells) or bFGF (100 ng/ml: HUVE cells), or preincubating virus with monoclonal antibodies (100 µg/ml) raised against bFGF (Transduction Laboratories, San Diego, USA) or VEGF (Sigma, Poole, UK), either alone or in combination (HUVE cells). The ability of adenovirus fibre knob domain to inhibit infection by the normal virus but not the retargeted virus shows that normal CAR-binding is not involved in infection of the retargeted virus. The failure of free bFGF to enhance transgene expression using non-retargeted virus shows that the ligand must be linked to the virus to promote infection. Inhibition of infection of HUVE cells by anti-bFGF and anti-VEGF antibodies, using bFGF and VEGF-targeted viruses, respectively, demonstrates that these ligands are responsible for the retargeted infection of HUVE cells.

Mouse A9 cells do not express CAR and are not susceptible to infection by normal adenovirus 5. In contrast, A9-21 cells have been engineered to express human CAR by introduction of human chromosome 21. As also shown in FIG. 10, normal adenovirus is unable to infect A9, although it can infect A9-21 cells. bFGF-retargeted polymer-coated virus, in contrast, infects both cell lines efficiently. This is a clear example of how adenovirus can be retargeted to infect via specific target-associated receptors, even if its normal receptor is not present.

Infection was also restored in SKOV3 human ovarian carcinoma cells using the same procedure for retargeting using bFGF. The level of infection achieved was substantially greater than for the unmodified virus. Infection was also restored using epidermal growth factor (EGF) and antibodies recognising Her2, Muc-1 and extracellular portions of the bFGF and EGF receptors (data not shown) as targeting ligands. Similarly, retargeting polymer-coated adenovirus using bFGF achieved high levels of gene expression in the primary ovarian cancer polyclonal cell "line" YSK19, grown in vitro for extended culture as shown by FIG. 11. The level of gene expression achieved in these cells was about 4-times greater than that achieved by the unmodified virus.

Example 16

Synthesis of Amino-Terminated poly(HPMA)

Amino-terminated poly(HPMA) polymers were prepared by radical polymerisation of HPMA in the presence of 2-aminoethanethiol.hydrochloride (AET) as the chain transfer agent. The polymers were obtained by 24 h polymerisation at 50° C. in methanol. Concentration of the reagents in the polymerisation mixture were as follows: HPMA 0.79 M, initiator AIBN $3.3 \times 10^{-3}$ M, AET $5 \times 10^{-3}$-$5 \times 10^{-2}$ M. The polymers with molecular weights in the range of 2000 to 20000 g/mol were isolated by precipitation into a 20-fold excess of acetone-diethylether (3:1). The molecular weights of the polymers were determined by FPLC on Superose 12™ column in 0.05 M TRIS buffer pH 8.0 containing 0.5 M NaCl as a mobile phase. The content of the terminal amino groups was determined by a colorimetric assay using 2,4,6-trinitrobenzenesulfonic acid.

Example 17

Synthesis of poly[(HPMA)-co-(Methacryloyl (MA)-Gly-Phe-Leu-Gly-ONp)]-graft-poly(HPMA)

Poly[(HPMA)-co-(MAGly-Phe-Leu-Gly-ONp)] was dissolved in dry DMSO and a calculated amount of amino-terminated poly(HPMA) was added to modify the required part of active ester groups. The solution was stirred for 12 hours at 25° C. The polymer was isolated by precipitation into a 20-fold excess of acetone-diethylether (3:1 by vol) and reprecipitated from 20% methanol solution into acetone.

The residual content of p-nitrophenyl active ester groups was determined by measuring UV absorption at 280 nm in DMSO. The obtained polymer was characterised (both number and weight average molecular weights) by FPLC equipped with on-line 18-angle light scattering detector WYATT.

Example 18

Synthesis of poly[(HPMA)-co-(MA-Gly-Phe-Leu-Gly-ONp)]-graft-oleylamine

Poly[(HPMA)-co-(MAGly-Phe-Leu-Gly-ONp)] was dissolved in dry DMSO and calculated amount of oleylamine was added to modify the required part of active ester groups. The solution was stirred for 2 hours at 25° C. The polymer was isolated by precipitation into 20-fold excess of acetone-diethylether (3:1 by vol) and reprecipitated from 20% methanol solution into acetone.

The residual content of p-nitrophenyl active ester groups was determined by measuring UV absorption at 280 nm in DMSO. The content of oleyl groups was estimated by $^1$H-NMR in DMSO-$d_6$ using the signal of the oleyl double bond (5.3 ppm). The obtained polymer was characterised (both number and weight average molecular weights) by FPLC equipped with on-line 18-angle light scattering detector produced by WYATT.

Example 19

Surface Modification of Vaccinia Virus with pHPMA-Gly-Gly-ONp Reduces Infectivity by Plaque Assay Vaccinia virus was selected as a representative member of the Pox virus family, to demonstrate surface modification using pHPMA-based multivalent polymers. Surface modification of Vaccinia virus with a multifunctional hydrophilic polymer can be measured by monitoring a reduction in natural infection activity. Infection activity can be subsequently restored to within one order of magnitude of wild type levels by incorporation of bFGF using the following protocol (Nb. it was found that low concentrations (<20 μg/ml) and brief sonication was necessary to reduce crosslinking of virus particles).

10 μg ($\sim 2.3 \times 10^9$) particles of Vaccinia virus in 100 μl of PBS and 50 mM HEPES pH 7.4 were treated with 100 μg of pHPMA-Gly-Gly-ONp for 1 hour on ice. 10 μg of bFGF was then added for a further 1 hour. Subsequently, 0.1% (vol/vol) aminoethanol was added to complete the reaction with any spare ester groups. Virus titer was measured by serial dilution of particles on 20 mm plates containing 75% confluent HeLa cells. Plaques were counted after 72 h with the aid of crystal violet staining.

Example 20

Surface Modification of Retrovirus Using pHPMA-Gly-Gly-ONp

To demonstrate surface modification of RNA-containing enveloped viruses, the retrovirus rv.AM12.LNC expressing nitroreductase (NTR) gene was selected. NTR expression increases the sensitivity of the cell line SKOV3 to a prodrug (CB1954) by converting it to the active bi-functional alkylating species; this resulting toxicity was used as a measure of infectivity. Surface modification of rv.AM12.LNC with pHPMA-Gly-Gly-ONp reduced NTR expression levels to below detectable levels. However, expression of NTR and sensitisation of SKOV3 cells to CB1954 was restored to within 50% of wild type levels after incorporation of bFGF using the following protocol.

Concentrated retrovirus particles, ($5 \times 10^6$ plaque forming units PFU) in 100 μl of PBS and 50 mM HEPES pH 7.4 were treated with 100 μg of pHPMA-Gly-Gly-ONp for 1 hour on ice. For retargeting modified viruses, 10 μg of bFGF was then added for a further 1 hour. After which, 0.1% (vol/vol) amino ethanol was added to complete the reaction with any spare ester groups. 500 ml of this preparation was diluted to 5 mls in DMEM containing 10% foetal calf serum supplemented with 2 mM glutamine and added to $10^6$ SKOV3 cells in a 10 cm plate in the presence of polybrene.

Example 21

Resistance to Inhibition by Neutralising Antibodies of Transfection Activity of Polymer-Coated Adenoviruses Retargeted Using bFGF in A549 Cells

As already shown, coating adenovirus with multifunctional hydrophilic polymer pHPMA-Gly-Gly-ONp prevents gene expression as recorded by the green fluorescence protein reporter gene. In this example, A549 cells were infected with $10^4$ particles/cell Ad5-GFP, or pHPMA-modified Ad5-GFP or bFGF-retargeted pHPMA-modified Ad5-GFP (prepared as described in Example 15) in the presence of various dilutions of rabbit anti-Ad5 serum. At 5 days post-infection GFP fluorescence was measured in the cells, and protein concentration determined. Infectivity of coated virus was restored by addition of bFGF. Neutralisation was reduced by less than 20% with retargeted coated virus compared with a reduction of 99.2% for Ad5-GFP alone.

Example 22

Retargeting of Adenovirus to Achieve Selective Infection of Receptor-Positive Target Cells in a Mixed Population

This Example demonstrated targeted infectivity within a mixed cell population, using pHPMA coated adenovirus retargeted with VEGF.

SUIT2 human pancreatic carcinoma cells and human umbilical vein endothelial (HUVE) cells were grown separately, trypsinised and resuspended in DMEM/2% FCS or M199/20% FCS respectively at a density of $5 \times 10^4$ cells/ml. Cells were mixed in equal numbers and after 2 h recovery at 37° C. virus was added ($10^4$ particles/cell) and incubated for a further 1.5 h before plating onto gelatin-coated 24 well plates. Phase contrast and fluorescence images were recorded at 48 h pi. These showed that the unmodified virus preferentially infects SUIT2 cells, while the VEGF-retargeted virus infects selectively HUVE cells.

Example 23

Retargeting Adenovirus to Achieve Receptor-Mediated Transfection of Target Cancer Cells In Vivo

$3 \times 10^6$ SUIT2 cells were injected into the peritoneal compartment of nude mice (Balb/C female, 6-8 wk) After 48 h, mice were administered $10^{10}$ particles of (A) unmodified adenovirus Adgfp$_{AE1}$; (B) polymer coated adenovirus pc-Adgfp$_{AE1}$; or (C) bFGF-retargeted polymer coated virus bFGF-pc-Adgfp$_{AE1}$; or (D) were administered $3 \times 10^9$ particles of bFGF-retargeted polymer coated virus bFGF-pc-Adgfp$_{AE}$ by the same route. After a further 48 h the animals were sacrificed and tumour cells recovered from the peritoneal compartment. GFP fluorescence was photographed using a Zeiss Axiovert 25 microscope, and the cells analysed by flow cytometry. Cells were gated against a negative control of SUIT2 cells, and a minimum fluorescence threshold set to include 0.1% control cells. The images obtained represented (A) 7.3% positive cells: mean fluorescence channels (MFC) 120.5; (B) 0.06% positive cells: MFC 6.0; (C) 8.69% positive cells: MFC 97.0; (D) 2.61% positive cells: MFC 64.0. Overall, this demonstrated that both unmodified virus (A) and bFGF-retargeted polymer-coated virus (C and D) have the ability to infect cells in vivo, but non-targeted polymer-coated viruses do not.

Example 24

Influence of Amount of Polymer Concentration on Infectivity of Coated Virus

Adenovirus 5 encoding the gene for β-galactosidase was reacted with amounts of reactive polymer pHPMA-GlyGly-ONp ranging from 200 µg/ml up to 20 mg/ml, for 1 h at room temperature before aminolysis of remaining reactive groups. The polymer-coated virus was then used to infect A549 cells, and levels of β-galactosidase gene expression were determined after 48 h. FIG. 13 shows that maximum inhibition of infection was achieved using polymer concentrations 5-10 mg/ml, which concentrations achieved 2-3 logs greater inhibition of infection than lower concentrations of polymer (200 µg/ml –2 mg/ml). When the polymer was aminolysed prior to adding it to the virus, no inhibition of infection was determined.

Example 25

Formulation of Adenovirus in Oils and Intra-Arterial Administration

25 µg ($8.6 \times 10^{10}$) of Ad5-GFP particles in 100 µl of PBS glycerol (10%) and 50 mM HEPES pH 7.4 was reacted with oleyl-modified reactive pHPMA (5 mg/ml, 1 h; the polymer was synthesised as described in Example 18). After aminolysis to remove unreacted groups the polymer-modified virus was freeze-dried and resuspended in lipiodol (an iodinated ester of poppyseed oil). The oily suspension was then injected via the hepatic artery to rabbits bearing intrahepatic VX2 carcinoma tumours. The accumulation and retention of the formulation within the tumour could be visualised by X-ray imaging. Animals were sacrificed after 48 h and substantial gene expression was determined within the tumour using fluorescence microscopy. Surrounding tissue showed no significant gene expression. A control provided by unmodified adenoviruses administered in PBS glycerol also achieved no significant transgene expression.

Example 26

Modification of Baculovirus Particles with pHPMA-Gly-Gly-ONp

Baculovirus particles were propagated using serum free adapted SF9 cells using the shaker culture (spinner cultures may also be used) procedure described by C. Richardson "Methods in Molecular Biology" Volume 39, Baculovirus Expression Protocols, Humana Press 1995. Budded virions (BVs) were purified from the cell suspension by centrifugation of cells into a pellet. The supernatant containing the BVs was concentrated and replaced with HBS using concentration dialysis with 300 KDa mwco membranes.

Concentrated baculovirus particles, ($5 \times 10^8$ particles/ml) in 100 µl of PBS and 50 mM HEPES pH 7.4 were treated with 500 µg of pHPMA-Gly-Gly-ONp for 2 hours on ice. For retargeting modified viruses, 10-100 µg of targeting ligand (bFGF) was then added for a further 1 hour. After that, 0.1% (vol/vol) amino ethanol was added to complete the reaction with any spare ester groups.

Example 27

Removal of Baculovirus Envelope Prior to Modification with pHPMA-Gly-Gly-ONp and Modification of Baculovirus Particles with pHPMA-Gly-Gly-ONp:

Purified baculovirus particles were produced and concentrated as in Example 26 above. The purified particles were then treated with 0.2% Triton ×100 for 15 minutes at room temperature to remove the baculovirus envelope.

The purified and concentrated baculovirus particles, without envelopes, were then processed and retargeted after polymer modification using exactly the same procedure as is described in Example 26.

Example 28

Modification of Baculovirus with a Multivalent Lipophilic Polymer poly[(HPMA)-co-(MAGly-Phe-Leu-Gly-ONp)]-graft-oleylamine.

As in Example 26 baculovirus particles were propagated using serum free adapted SF9 cells using the shaker culture procedure mentioned therein and were purified from the cell suspension by centrifugation of cells into a pellet. The supernatant containing the BVs was then concentrated and replaced with DMSO using concentration dialysis with 300 KDa mwco membranes.

The concentrated baculovirus particles, ($5 \times 10^8$ particles/ml) in 100 µl of dry DMSO were treated next with 500 µg of poly[(HPMA)-co-(MAGly-Phe-Leu-Gly-ONp)]-graft-oleylamine (see Example 18) for 2 hours on ice. After that, 0.1% (vol/vol) amino ethanol was added to complete the reaction with any spare ester groups.

The virus particles modified in this way should be retained in non-aqueous liquids (oils) by phase separation. A formulation of oil, such as olive corn or sunflower oil, containing such polymer modified virus particles, or bacteria or spores could be applied to plant surfaces by spray. Such applications, used for example in connection with pest control, should persist for longer periods in the field due to resistance against desiccation and removal by rain. Additionally, formulations or this kind could be applied to standing water, permitting distribution of Baculovirus over a wide area with ease, for use against populations of malarial larvae for example.

Example 29

Modification of *Bacillus thuringiensis* with poly [(HPMA)-co-(MAGly-Phe-Leu-Gly-ONp)]-graft-oleylamine.

In this example concentrated *Bacillus thuringiensis* ($5 \times 10^9$ particles/ml) in 100 µl of dry DMSO were treated with 1000 µg of poly[(HPMA)-co-(MAGly-Phe-Leu-Gly-ONp)]-graft-oleylamine (Example 18) for 4 hours on ice. After that, 0.1% (vol/vol) amino ethanol was added to complete the reaction with any spare ester groups. As with the modified baculovirus of Example 28, the bacterium (or spores thereof) should be retained in non-aqueous liquids (oils) by phase separation, and a formulation of oil, such as olive corn or sunflower oil, containing the polymer modified bacterium/spore could be applied to plant surfaces by spray. Again, such application would persist for longer periods in the field due to resistance against desiccation and removal by rain, and again the formulation could be applied to standing water, permitting distribution of *Bacillus thuringiensis* over a wide area with ease, for use against populations of malarial larvae.

Example 30

Modification of *Pseudomonas* sp. with pHPMA-Gly-Gly-ONp:

An oil degrading isolate of *Pseudomonas fluorescens* was propagated in vitro using tryptone soy broth, and oil degrading activity was selected for by growth in artificial sea water supplemented with 0.1% diesel oil.

Concentrated *Pseudomonas fluorescens* cells ($5 \times 10^9$ cells/ml) were washed in PBS, and re-suspended in PBS containing 50 mM HEPES pH 7.4. The cells were then treated with 10 mg/ml of pHPMA-Gly-Gly-ONp for 8 hours on ice while slowly stirring. After that, 0.1% (vol/vol) amino ethanol was added to complete the reaction with any spare ester groups.

*Pseudomonas* sp. modified in this way is provided with an increased hydrated layer, thereby allowing more efficient aerobic metabolism in a crude oil suspension.

Example 31

Modification of *Pseudomonas* sp. with (poly[(HPMA)-co-(MAGly-Phe-Leu-Gly-ONp)]-graft-oleylamine).

Concentrated *Pseudomonas fluorescens*, ($2 \times 10^8$/ml) in 100 µl of dry DMSO supplemented with diethylamine (to increase basicity) were treated with 100 µg of (poly [(HPMA)-co-(MAGly-Phe-Leu-Gly-ONp)]-graft-oleylamine) for 4 hour on ice. 0.1% (vol-vol) amino ethanol was then added to complete the reaction with any spare ester groups. The resulting polymer-modified bacterium shows enhanced solubility in non-aqueous solvents, notably oils. Bacteria modified in this way will generally have greater retention in crude oil slicks resulting in an improved specific activity for bioremediation.

Example 32

Modification and Retargeting of Bacteriophage M13

Bacteriophage M13 was propagated in *E. Coli* strain ER2537 in LB medium. Phage were purified in a known manner by precipitation using poly(ethylene glycol) as described in the protocol from New England Biolabs, and were then returned to Hepes-buffered saline (pH 7.8) by dialysis. The phage were then modified by reaction with pHPMA-Gly-Gly-NHS, with the reaction being monitored by measuring the falling absorption at 274 nm. After 1 h the phage was retargeted by addition of herceptin (a monoclonal antibody recognising the HER2 proto-oncogene), allowing linkage of the herceptin to spare reactive esters on the polymer-modified phage. After purification the resulting retargeted phage showed over 100-times increased rates of accumulation by HER2-positive cells.

As will be seen, the invention presents a number of different aspects and it embraces within its scope all novel and inventive features and aspects herein disclosed, either explicitly or implicitly and either singly or in combination with one another. Also, many modifications are possible and, in particular, the scope of the invention is not to be construed as being limited by the illustrative examples or by the terms and expressions used herein merely in a descriptive or explanatory sense.

The invention claimed is:

1. A method for modifying the biological and/or physicochemical properties of a biological element, said method comprising reacting said biological element with a synthetic hydrophilic multivalent polymer comprising:
   (i) a polymer backbone based upon monomer units selected from the group consisting of N-2-hydroxypropylmethacrylamide (HPMA), N-(2-Hydroxy ethyl)-L-Glutamine (HEG), ethyleneglycol-oligopeptide and dextran monomers; and
   (ii) multiple reactive groups,
wherein the biological element is linked to the polymer by a plurality of linkages.

2. A method as claimed in claim 1 wherein the biological element is an infectious agent that normally targets and interacts with particular sites or receptors in a host, wherein the polymer modification has the effect of modifying the infectivity of the biological element and/or retargeting it to a new or different site or receptor in the host.

3. A method as claimed in claim 2 wherein the infectious agent is a viral vector containing therapeutic genetic material.

4. A method as claimed in claim 2 wherein retargeting is achieved by incorporating a specific targeting group or moiety in the multivalent polymer and by ensuring that after modification the biological element is sufficiently coated with the polymer as to inhibit targeting and interaction with the original target site or receptor of the host.

5. A method as claimed in claim 1 which has the effect of modifying the solubility or partition co-efficient characteristics of the biological element in non-aqueous media by virtue of a hydrophobic group incorporated in the polymer.

6. A polymer modified biological element in which the biological element is covalently linked to a synthetic hydrophilic multivalent polymer comprising:
   (i) a polymer backbone based upon monomer units selected from the group consisting of N-2-hydroxypropylmethacrylamide (HPMA), N-(2-Hydroxy ethyl)-L-Glutamine (HEG), ethyleneglycol-oligopeptide and dextran monomers; and
   (ii) multiple reactive groups,
wherein said polymer is linked to the biological element by at least two covalent linkages.

7. A polymer modified biological element according to claim 6 wherein the biological element includes therapeutic genetic material.

8. A polymer modified biological element according to claim 6 wherein the number of linkages between the polymer and the biological element is greater than three.

9. A polymer modified biological element according to claim 6 wherein the linkage of said polymer to the biological element and modification of the latter results in the inhibition of the ability of the biological element to interact in a host biological system with other molecules with which it would otherwise normally interact or in the inhibition of the ability of the biological element to bind to sites or receptors to which it would otherwise normally bind.

10. A polymer modified biological element according to claim 6 wherein each of the reactive groups is connected to the polymer backbone either directly or via a spacer group.

11. A polymer modified biological element according to claim 6 wherein the polymer and/or the linkages between it and the biological element are hydrolytically or enzymatically degradable.

12. A polymer modified biological element according to claim 6 wherein the polymer used to modify the biological element is cross-linked such that it forms a hydrogel.

13. A polymer modified biological element according to claim 6 wherein a biologically active agent is coupled to or included in the polymer.

14. A polymer modified biological element according to claim 13 wherein the biologically active agent is one or more of the following: a growth factor or cytokine, a sugar, a hormone, a lipid, a phospholipid, a fat, an apolipoprotein, a cell adhesion promoter, an enzyme, a toxin, a peptide, a glycoprotein, a serum protein, a vitamin, a mineral, and an antibody recognizing receptor.

15. A polymer modified biological element according to claim 13 wherein the biological active agent is an antibody or antibody fragment.

16. A polymer modified biological element according to claim 15 wherein said antibody and antibody fragments are monoclonal.

17. A polymer modified biological element as claimed in claim 6 wherein the biological element is a virus or other infective micro-organism and wherein the polymer is effective to bring about substantially a complete loss of the infectivity of the unmodified biological element.

18. A polymer modified biological element as claimed in claim 6 wherein the modification of the biological element has the effect of retargeting the biological element to different receptors in a biological host.

19. A polymer modified biological element as claimed in claim 6 wherein the modification of the biological element has the effect of modifying the solubility and dispersal and stability characteristics of the biological element within a non-aqueous environment.

20. A polymer modified biological element as claimed in claim 6 wherein the biological element is a micro-organism having oil degradative activity.

21. A polymer modified biological element as claimed in claim 6 wherein the polymer incorporates an oleyl or a hydrophobic group.

22. A polymer modified biological element as claimed in claim 6 wherein the biological element is a baculovirus particle.

23. A process for the preparation of a polymer modified biological element as defined in claim 6 which process comprises combining a biological element with a polymer.

24. A polymer modified biological element obtainable by the process according to claim 23.

25. A composition comprising a polymer modified biological element as defined in claim 6 in association with a carrier.

26. A composition as claimed in claim 25 wherein the carrier is a pharmaceutically acceptable additive, diluent or excipients.

27. A method of treatment of oil pollutants comprising contacting a polymer modified biological element as claimed in claim 20 with said oil pollutants.

28. A method of treating a pathogen comprising contacting said pathogen with a polymer modified biological element as claimed in claim 6, wherein said biological element is a biological pesticide.

29. A polymer modified biological element as claimed in claim 6 wherein the biological element is an adenovirus.

30. A polymer modified biological element in which the biological element is covalently linked to a synthetic hydrophilic multivalent polymer comprising:
   (i) a polymer backbone based upon monomer units selected from the group consisting of N-2-hydroxypropylmethacrylamide (HPMA), N-(2-Hydroxy ethyl)-L-Glutamine (HEG), ethyleneglycol-oligopeptide and dextran monomers; and
   (ii) multiple reactive groups,
   wherein the biological element is linked to the polymer by a plurality of linkages, and
   wherein the biological element is an infectious agent that normally targets and interacts with particular sites or receptors in a host, wherein the polymer modification has the effect of modifying the infectivity of the biological element and/or retargeting it to a new or different site or receptor in the host, wherein retargeting is achieved by incorporating a specific targeting group or moiety in the multivalent polymer and by ensuring that after modification the biological element is sufficiently coated with the polymer as to inhibit targeting and interaction with the original target site or receptor of the host.

31. A method for modifying the biological and/or physicochemical properties of a biological element, said method comprising reacting said biological element with a synthetic hydrophilic multivalent polymer having multiple reactive groups wherein the biological element is linked to the polymer by a plurality of linkages comprising:
   (i) a polymer backbone based upon monomer units selected from the group consisting of N-2-hydroxypropylmethacrylamide (HPMA), N-(2-Hydroxy ethyl)-L-Glutamine (HEG), ethyleneglycol-oligopeptide and dextran monomers; and
   (ii) multiple reactive groups,
   wherein the biological element is linked to the polymer by a plurality of linkages, and
   wherein the biological element is an infectious agent that normally targets and interacts with particular sites or receptors in a host, wherein the polymer modification has the effect of modifying the infectivity of the biological element and/or retargeting it to a new or different site or receptor in the host, wherein retargeting is achieved by incorporating a specific targeting group or moiety in the multivalent polymer and by ensuring that after modification the biological element is sufficiently coated with the polymer as to inhibit targeting and interaction with the original target site or receptor of the host.

32. A method of delivering a biological element to the cell of an individual comprising administering to the individual a polymer modified form of said biological element wherein said polymer modified biological element is as claimed in claim 6.

33. A method of delivering a biological element to the cell of an individual comprising administering to the individual a polymer modified form of said biological element wherein said polymer modified biological element is as claimed in claim 30.

34. A pharmaceutical composition comprising a polymer modified biological element as claimed in claim 6, and a physiologically acceptable carrier or diluent.

35. A pharmaceutical composition comprising a polymer modified biological element as claimed in claim 6, and a physiologically acceptable carrier or diluent.

* * * * *

UNITED STATES PATENT AND TRADEMARK OFFICE
CERTIFICATE OF CORRECTION

| | | |
|---|---|---|
| PATENT NO. | : 7,279,318 B1 | Page 1 of 1 |
| APPLICATION NO. | : 10/009347 | |
| DATED | : October 9, 2007 | |
| INVENTOR(S) | : Leonard C. W. Seymour et al. | |

It is certified that error appears in the above-identified patent and that said Letters Patent is hereby corrected as shown below:

Claim 35, line 2 (column 32, line 45), replace "claim 6" with --claim 30--.

Signed and Sealed this

Second Day of June, 2009

JOHN DOLL
*Acting Director of the United States Patent and Trademark Office*